United States Patent
Cook et al.

(10) Patent No.: US 10,172,853 B2
(45) Date of Patent: *Jan. 8, 2019

(54) METHOD OF THERAPEUTIC ADMINISTRATION OF DHE TO ENABLE RAPID RELIEF OF MIGRAINE WHILE MINIMIZING SIDE EFFECT PROFILE

(71) Applicant: MAP Pharmaceuticals, Inc., Irvine, CA (US)

(72) Inventors: Robert O. Cook, Hillsborough, NJ (US); Stephen B. Shrewsbury, Kirkland, WA (US); Nabih N. Ramadan, Lake Forest, IL (US); Thomas A. Armer, Los Altos, CA (US)

(73) Assignee: MAP PHARMACEUTICALS, INC., Irvine, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/471,334

(22) Filed: Mar. 28, 2017

(65) Prior Publication Data

US 2017/0196861 A1 Jul. 13, 2017

Related U.S. Application Data

(63) Continuation of application No. 14/921,860, filed on Oct. 23, 2015, now Pat. No. 9,833,451, which is a continuation of application No. 14/514,322, filed on Oct. 14, 2014, now abandoned, which is a continuation of application No. 13/406,391, filed on Feb. 27, 2012, now abandoned, which is a continuation of application No. 12/069,667, filed on Feb. 11, 2008, now Pat. No. 8,148,377.

(60) Provisional application No. 60/900,850, filed on Feb. 11, 2007.

(51) Int. Cl.
   *A61K 31/4985* (2006.01)
   *A61K 9/00* (2006.01)
   *A61K 31/48* (2006.01)
   *A61K 31/10* (2006.01)

(52) U.S. Cl.
   CPC ........ *A61K 31/4985* (2013.01); *A61K 9/0073* (2013.01); *A61K 9/0075* (2013.01); *A61K 31/10* (2013.01); *A61K 31/48* (2013.01)

(58) Field of Classification Search
   CPC . A61K 31/4985; A61K 9/0073; A61K 9/0075
   See application file for complete search history.

(56) References Cited

U.S. PATENT DOCUMENTS

| | | |
|---|---|---|
| 2,868,691 A | 1/1959 | Porush et al. |
| 2,885,427 A | 5/1959 | Ruh et al. |
| 3,014,844 A | 12/1961 | Thiel et al. |
| 3,219,533 A | 11/1965 | Mullins et al. |
| 3,261,748 A | 7/1966 | Larsen |
| 3,320,125 A | 5/1967 | Grim |
| 3,644,353 A | 2/1972 | Lunte et al. |
| 3,809,294 A | 5/1974 | Torgeson |
| 3,897,779 A | 8/1975 | Hansen |
| 3,994,421 A | 11/1976 | Hansen |
| 4,044,126 A | 8/1977 | Cook et al. |
| 4,129,603 A | 12/1978 | Bell |
| 4,174,295 A | 11/1979 | Bargiga et al. |
| 4,241,048 A | 12/1980 | Durbak et al. |
| 4,294,829 A | 10/1981 | Suzuki et al. |
| 4,311,863 A | 6/1982 | Gumprecht |
| 4,335,121 A | 6/1982 | Phillips et al. |
| 4,347,236 A | 8/1982 | Tanskanen |
| 4,352,789 A | 10/1982 | Thiel |
| 4,364,923 A | 12/1982 | Cook et al. |
| 4,405,598 A | 9/1983 | Brown |
| 4,414,209 A | 11/1983 | Cook et al. |
| 4,423,099 A | 12/1983 | Mueller et al. |
| 4,462,983 A | 7/1984 | Azrla et al. |
| 4,514,574 A | 4/1985 | Inoue et al. |
| 4,524,769 A | 6/1985 | Wetterlin |

(Continued)

FOREIGN PATENT DOCUMENTS

| | | |
|---|---|---|
| BE | 1006872 A6 | 1/1995 |
| CA | 2075058 C | 8/1991 |

(Continued)

OTHER PUBLICATIONS

Diener, Hans Christoph. A Review of Current Treatments for Migraine, Eur Neurol 1994, 34(2):18-25.

Humbert et al (Sep. 1996). "Human pharmacokinetic of dihydroergotamine administered by nasal spray," Clinical Pharmacology and Therapeutics 60(3): 285275.

Johnson, K.W. et al. (1998). "Seroconin in Migraine: Theories, Animal Models and Emerging Therapies," vol. 51 in Progress in Drug Research, Jucker, E. ed., Birkhäuser Verlag: Basel, Germany, pp. 221-244.

(Continued)

*Primary Examiner* — James D Anderson

(74) *Attorney, Agent, or Firm* — Lorenz Siddiqi

(57) ABSTRACT

Pharmaceutical compositions containing dihydroergotamine (DHE) and methods in which DHE is administered to patients for treatment of migraine without side effects or adverse effects are disclosed. Methods for rapid treatment of migraine with DHE are disclosed comprising: dampening the peak plasma concentration ($C_{max}$) and slightly delaying the peak such as to avoid activating the dopaminergic and adrenergic receptors, while achieving sufficient active binding to the serotonin receptors to provide relief from migraine symptoms within a timeframe that permits rapid resolution of migraine symptoms. Inhaler devices suitable for the methods are disclosed. Kits for practicing the methods of invention are disclosed.

17 Claims, 8 Drawing Sheets

(56) References Cited

U.S. PATENT DOCUMENTS

| | | |
|---|---|---|
| 4,582,731 A | 4/1986 | Smith |
| 4,590,206 A | 5/1986 | Forrester et al. |
| 4,650,810 A | 3/1987 | Bays et al. |
| 4,659,696 A | 4/1987 | Hiral et al. |
| 4,670,419 A | 6/1987 | Uda et al. |
| 4,710,495 A | 12/1987 | Bodor |
| 4,737,384 A | 4/1988 | Murthy et al. |
| 4,767,612 A | 8/1988 | Hagen et al. |
| 4,810,488 A | 3/1989 | Jinka |
| 4,814,161 A | 3/1989 | Jinks et al. |
| 4,851,595 A | 7/1989 | Gumprecht |
| 4,859,696 A | 8/1989 | Kamiya et al. |
| 4,866,051 A | 9/1989 | Hunt et al. |
| 4,884,565 A | 12/1989 | Cocozza |
| 4,914,125 A | 4/1990 | Baldinger et al. |
| 4,916,125 A | 4/1990 | Herrling et al. |
| 4,923,720 A | 5/1990 | Lee et al. |
| 4,940,171 A | 7/1990 | Gilroy |
| 4,945,119 A | 7/1990 | Smits et al. |
| 4,963,557 A | 10/1990 | Badger et al. |
| 4,970,093 A | 12/1990 | Slavers et al. |
| 4,994,483 A | 2/1991 | Oxford et al. |
| 5,011,678 A | 4/1991 | Wang et al. |
| 5,021,428 A | 6/1991 | Carr et al. |
| 5,043,280 A | 8/1991 | Fischer et al. |
| 5,066,522 A | 11/1991 | Cole et al. |
| 5,106,659 A | 4/1992 | Hastings et al. |
| 5,118,494 A | 4/1992 | Schlutz et al. |
| 5,126,123 A | 6/1992 | Johnson |
| 5,130,137 A | 7/1992 | Crowley, Jr. |
| 5,145,684 A | 9/1992 | Liversidge et al. |
| 5,176,878 A | 1/1993 | Wehling et al. |
| 5,182,040 A | 1/1993 | Bartlett et al. |
| 5,182,097 A | 1/1993 | Byron et al. |
| 5,186,164 A | 2/1993 | Raghuprasad |
| 5,192,528 A | 3/1993 | Radhakrishnan et al. |
| 5,196,575 A | 3/1993 | Sebastian |
| 5,200,413 A | 4/1993 | King et al. |
| 5,202,110 A | 4/1993 | Dalby et al. |
| 5,206,268 A | 6/1993 | Weymans et al. |
| 5,221,731 A | 6/1993 | Wehling et al. |
| 5,225,163 A | 7/1993 | Purewal et al. |
| 5,229,486 A | 7/1993 | Paul et al. |
| 5,230,884 A | 7/1993 | Evans et al. |
| 5,232,707 A | 8/1993 | Lokenagard |
| 5,242,949 A | 9/1993 | Goldberg et al. |
| 5,248,684 A | 9/1993 | Suzuki et al. |
| 5,254,330 A | 10/1993 | Ganderton et al. |
| 5,254,755 A | 10/1993 | Li et al. |
| 5,270,305 A | 12/1993 | Plamer |
| 5,273,759 A | 12/1993 | Simmons |
| 5,290,539 A | 3/1994 | Marecid |
| 5,292,499 A | 3/1994 | Evans et al. |
| 5,302,581 A | 4/1994 | Sarin et al. |
| 5,310,762 A | 5/1994 | Latter et al. |
| 5,314,682 A | 5/1994 | Sweval et al. |
| 5,317,103 A | 5/1994 | Baker et al. |
| 5,320,094 A | 6/1994 | Laube et al. |
| 5,320,714 A | 6/1994 | Brendel |
| 5,331,953 A | 7/1994 | Andersson et al. |
| 5,348,730 A | 9/1994 | Greenleaf et al. |
| 5,354,934 A | 10/1994 | Pitt et al. |
| 5,364,838 A | 11/1994 | Rubsamen |
| 5,364,863 A | 11/1994 | Cohen et al. |
| 5,376,359 A | 12/1994 | Johnson |
| 5,376,386 A | 12/1994 | Gnaderson et al. |
| 5,384,133 A | 1/1995 | Boyes et al. |
| 5,399,574 A | 3/1995 | Robertson et al. |
| 5,424,076 A | 6/1995 | Gorlssen et al. |
| 5,427,282 A | 6/1995 | Greenleaf et al. |
| 5,434,154 A | 7/1995 | Smith et al. |
| 5,437,798 A | 8/1995 | LaRoche et al. |
| 5,439,670 A | 8/1995 | Purewal et al. |
| 5,441,969 A | 8/1995 | Axelsson et al. |
| 5,458,135 A | 10/1995 | Patton et al. |
| 5,464,632 A | 11/1995 | Cousin et al. |
| 5,464,864 A | 11/1995 | King et al. |
| 5,466,699 A | 11/1995 | Robertson et al. |
| 5,468,768 A | 11/1995 | Cipollina et al. |
| 5,474,759 A | 12/1995 | Fassberg et al. |
| 5,491,148 A | 2/1996 | Berger et al. |
| 5,492,688 A | 2/1996 | Byron et al. |
| 5,506,023 A | 4/1996 | Byron et al. |
| 5,518,998 A | 6/1996 | Bäckström et al. |
| 5,560,543 A | 10/1996 | Smith et al. |
| 5,605,674 A | 2/1997 | Purewal et al. |
| 5,607,697 A | 3/1997 | Alkire et al. |
| 5,617,293 A | 4/1997 | Schulze et al. |
| 5,619,984 A | 4/1997 | Hodson et al. |
| 5,620,631 A | 4/1997 | Halskel et al. |
| 5,639,441 A | 6/1997 | Sievera et al. |
| 5,639,475 A | 6/1997 | Bettman et al. |
| 5,648,004 A | 7/1997 | Simpson |
| 5,653,962 A | 8/1997 | Akehurst et al. |
| 5,658,549 A | 8/1997 | Akehurst et al. |
| 5,674,471 A | 10/1997 | Akehurst et al. |
| 5,674,472 A | 10/1997 | Akehurst et al. |
| 5,674,473 A | 10/1997 | Purewal et al. |
| 5,676,929 A | 10/1997 | Akehurst et al. |
| 5,681,545 A | 10/1997 | Purewal et al. |
| 5,683,676 A | 11/1997 | Akehurst et al. |
| 5,683,677 A | 11/1997 | Purewal et al. |
| 5,688,782 A | 11/1997 | Neale et al. |
| 5,695,743 A | 12/1997 | Purewal et al. |
| 5,696,744 A | 12/1997 | Okamoto et al. |
| 5,707,634 A | 1/1998 | Schmitt |
| 5,708,039 A | 1/1998 | Daly et al. |
| 5,709,886 A | 1/1998 | Bettman et al. |
| 5,720,940 A | 2/1998 | Purewal et al. |
| 5,725,836 A | 3/1998 | Rouanet et al. |
| 5,736,124 A | 4/1998 | Akehurst et al. |
| 5,740,793 A | 4/1998 | Hodson et al. |
| 5,744,123 A | 5/1998 | Merkus |
| 5,756,483 A | 5/1998 | Merkus |
| 5,766,573 A | 6/1998 | Purewal et al. |
| 5,770,559 A | 6/1998 | Manning et al. |
| 5,776,432 A | 7/1998 | Schultz et al. |
| 5,776,434 A | 7/1998 | Purewal et al. |
| 5,776,491 A | 7/1998 | Allen, Jr. et al. |
| 5,776,573 A | 7/1998 | Trotter et al. |
| 5,795,594 A | 8/1998 | York et al. |
| 5,807,576 A | 9/1998 | Allen, Jr. et al. |
| 5,807,578 A | 9/1998 | Acosta-Cuallo et al. |
| 5,813,597 A | 9/1998 | Wakevainen |
| 5,833,950 A | 11/1998 | Taylor et al. |
| 5,849,265 A | 12/1998 | Li-Bovet et al. |
| 5,851,453 A | 12/1998 | Hanna et al. |
| 5,874,029 A | 2/1999 | Subramaniam et al. |
| 5,874,064 A | 2/1999 | Edwards et al. |
| 5,875,766 A | 3/1999 | Ozawa |
| 5,875,776 A | 3/1999 | Vaghefi |
| 5,916,125 A | 6/1999 | Snyder |
| 5,916,540 A | 6/1999 | Akehurst et al. |
| 5,919,435 A | 7/1999 | Taylor et al. |
| 5,922,306 A | 7/1999 | Akehurst et al. |
| 5,922,355 A | 7/1999 | Parikh et al. |
| 5,922,675 A | 7/1999 | Baker et al. |
| 5,939,425 A | 8/1999 | Caruso |
| 5,942,251 A | 8/1999 | Markus |
| 5,954,047 A | 9/1999 | Armer et al. |
| 5,955,439 A | 9/1999 | Green |
| 5,972,388 A | 10/1999 | Sakon et al. |
| 5,997,848 A | 12/1999 | Patton et al. |
| 6,006,745 A | 12/1999 | Marecki |
| 6,012,454 A | 1/2000 | Hodson et al. |
| 6,013,245 A | 1/2000 | Taylor et al. |
| 6,024,981 A | 2/2000 | Khankari et al. |
| 6,026,808 A | 2/2000 | Armer et al. |
| 6,030,682 A | 2/2000 | Marecki |
| 6,043,244 A | 3/2000 | Caruso |
| 6,054,488 A | 4/2000 | Oliver et al. |
| 6,063,138 A | 5/2000 | Hanna et al. |
| 6,063,910 A | 5/2000 | Debanedetti et al. |
| 6,068,832 A | 5/2000 | Berry et al. |

(56) References Cited

U.S. PATENT DOCUMENTS

| | | |
|---|---|---|
| 6,077,539 A | 6/2000 | Plachetka et al. |
| 6,089,911 A | 7/2000 | Goto et al. |
| 6,095,141 A | 8/2000 | Armer et al. |
| 6,098,619 A | 8/2000 | Britto et al. |
| 6,117,455 A | 9/2000 | Takadea et al. |
| 6,119,853 A | 9/2000 | Garrill et al. |
| 6,120,613 A | 9/2000 | Romack et al. |
| 61,236,924 | 9/2000 | Mistry et al. |
| 6,129,905 A | 10/2000 | Cutle |
| 6,131,566 A | 10/2000 | Ashurst et al. |
| 6,136,295 A | 10/2000 | Edwards et al. |
| 6,143,277 A | 11/2000 | Ashurst et al. |
| 6,149,892 A | 11/2000 | Britto |
| 6,149,941 A | 11/2000 | Schwarz et al. |
| 6,153,173 A | 11/2000 | Sapsford et al. |
| 6,156,339 A | 12/2000 | Grother et al. |
| 6,179,118 B1 | 1/2001 | Garrill et al. |
| 6,183,782 B1 | 2/2001 | Hallworth |
| 6,190,029 B1 | 2/2001 | Taniuchi et al. |
| 6,200,293 B1 | 3/2001 | Kriesel et al. |
| 6,200,549 B1 | 3/2001 | Akehurst et al. |
| 6,221,339 B1 | 4/2001 | Akehurst et al. |
| 6,236,647 B1 | 5/2001 | Akehurst et al. |
| 6,251,368 B1 | 6/2001 | Akehurst et al. |
| 6,253,762 B1 | 7/2001 | Britto |
| 6,264,981 B1 | 7/2001 | Zhang et al. |
| 6,284,267 B1 | 9/2001 | Sarlikiotis et al. |
| 6,290,991 B1 | 9/2001 | Roser et al. |
| 6,303,103 B1 | 10/2001 | Akehurst et al. |
| 6,306,368 B1 | 10/2001 | Taylor et al. |
| 6,306,369 B1 | 10/2001 | Akehurst et al. |
| 6,309,623 B1 | 10/2001 | Weers et al. |
| 6,309,624 B1 | 10/2001 | Sapsford et al. |
| 6,316,029 B1 | 11/2001 | Jain et al. |
| 6,331,310 B1 | 12/2001 | Roser et al. |
| 6,333,023 B1 | 12/2001 | Akehurst et al. |
| 6,346,232 B1 | 2/2002 | Schultz et al. |
| 6,346,323 B1 | 2/2002 | Nettesheim |
| 6,352,684 B1 | 3/2002 | Purewal et al. |
| 6,367,471 B1 | 4/2002 | Genosar et al. |
| 6,390,291 B1 | 5/2002 | Garrill et al. |
| 6,395,299 B1 | 5/2002 | Babich et al. |
| 6,395,300 B1 | 5/2002 | Siraub et al. |
| 6,406,681 B1 | 6/2002 | Adjei et al. |
| 6,413,497 B1 | 7/2002 | Well et al. |
| 6,416,743 B1 | 7/2002 | Fassberg et al. |
| 6,419,899 B1 | 7/2002 | Well et al. |
| 6,440,337 B1 | 8/2002 | Hanna et al. |
| 6,451,287 B1 | 9/2002 | Desimone et al. |
| 6,495,535 B1 | 12/2002 | Plachetka et al. |
| 6,503,480 B1 | 1/2003 | Edwards et al. |
| 6,503,482 B1 | 1/2003 | Fassberg et al. |
| 6,514,482 B1 | 2/2003 | Bartus et al. |
| 6,527,151 B1 | 3/2003 | Pavkov et al. |
| 6,558,651 B1 | 5/2003 | Riebe et al. |
| 6,585,958 B1 | 7/2003 | Keller et al. |
| 6,613,307 B1 | 9/2003 | Cooper |
| 6,613,308 B2 | 9/2003 | Bartus et al. |
| 6,656,453 B2 | 12/2003 | Riebe et al. |
| 6,656,492 B2 | 12/2003 | Riebe et al. |
| 6,685,951 B2 | 2/2004 | Cutler |
| 6,743,413 B1 | 8/2004 | Schultz et al. |
| 6,858,199 B1 | 2/2005 | Edwards et al. |
| 6,860,907 B1 | 3/2005 | Hanna et al. |
| 6,884,408 B2 | 4/2005 | Rabinowitz et al. |
| 6,979,437 B2 | 12/2005 | Bartus et al. |
| 7,060,694 B2 | 6/2006 | Plachetka et al. |
| 7,087,197 B2 | 8/2006 | Palakodaty et al. |
| RE39,847 E | 9/2007 | Adjei et al. |
| RE40,045 E | 2/2008 | Palmer |
| 7,994,197 B2 | 8/2011 | Cook et al. |
| 8,119,639 B2 | 2/2012 | Cook et al. |
| 8,148,377 B2 | 4/2012 | Cook et al. |
| 9,833,451 B2 * | 12/2017 | Cook ................ A61K 31/4985 |
| 2001/0053913 A1 | 12/2001 | Freedland |
| 2002/0000681 A1 | 1/2002 | Gupta et al. |
| 2002/0035993 A1 | 3/2002 | Edwards et al. |
| 2002/0071812 A1 | 6/2002 | Well et al. |
| 2002/0081266 A1 | 6/2002 | Woolfe et al. |
| 2002/0114844 A1 | 8/2002 | Hanna et al. |
| 2003/0008005 A1 | 1/2003 | Cutler |
| 2003/0017175 A1 | 1/2003 | Cutler |
| 2003/0017994 A1 | 1/2003 | Cutler |
| 2003/0022910 A1 | 1/2003 | Cutler |
| 2003/0040537 A1 | 2/2003 | Plachetka et al. |
| 2003/0047824 A1 | 3/2003 | Hanna et al. |
| 2003/0081513 A1 | 6/2003 | Moheen et al. |
| 2003/0086970 A1 | 6/2003 | Woolfe et al. |
| 2003/0109421 A1 | 8/2003 | Palakodaty et al. |
| 2003/0114476 A1 | 8/2003 | Plachetka et al. |
| 2003/0170310 A1 | 9/2003 | Wadhwa |
| 2003/0175214 A1 | 9/2003 | Staniforth et al. |
| 2003/0181462 A1 | 9/2003 | Dooda et al. |
| 2003/0198669 A1 | 10/2003 | Cutler |
| 2003/0223939 A1 | 12/2003 | Kordikowald et al. |
| 2004/0071783 A1 | 4/2004 | Hanna et al. |
| 2004/0119179 A1 | 8/2004 | Perrut et al. |
| 2004/0119178 A1 | 9/2004 | Cutler |
| 2004/0197273 A1 | 10/2004 | Schultz et al. |
| 2005/0170000 A1 | 8/2005 | Walker et al. |
| 2005/0181041 A1 | 8/2005 | Goldman |
| 2005/0206023 A1 | 9/2005 | Hanna et al. |
| 2006/0014774 A1 | 1/2006 | Flieger et al. |
| 2006/0147389 A1 | 7/2006 | Staniforth et al. |
| 2006/0240043 A1 | 10/2006 | Meyerson et al. |
| 2006/0246070 A1 | 11/2006 | Heavner et al. |
| 2007/0202054 A1 | 8/2007 | Pipkin et al. |
| 2007/0253913 A1 | 11/2007 | Mohsen et al. |
| 2008/0118442 A1 | 5/2008 | Mohsen et al. |
| 2008/0287451 A1 | 11/2008 | Cook et al. |
| 2009/0232698 A1 | 9/2009 | Pattersson et al. |
| 2009/0291050 A1 | 11/2009 | Kordikowski et al. |
| 2010/0015184 A1 | 1/2010 | Tuel |
| 2010/0029665 A1 | 2/2010 | Meyerson et al. |
| 2010/0081663 A1 | 4/2010 | Cook et al. |
| 2010/0081664 A1 | 4/2010 | Cook et al. |
| 2010/0284940 A1 | 11/2010 | Cook et al. |
| 2010/0288275 A1 | 11/2010 | Jhamandas et al. |
| 2011/0118189 A1 | 5/2011 | Farr et al. |

FOREIGN PATENT DOCUMENTS

| | | |
|---|---|---|
| CA | 2062854 A1 | 9/1992 |
| DE | 2703119 A1 | 8/1977 |
| DE | 2737132 A1 | 2/1978 |
| DE | 3018550 A1 | 12/1980 |
| DE | 4041563 A1 | 6/1992 |
| DK | 1349236 B | 2/1977 |
| EP | 0 039 369 A1 | 11/1981 |
| EP | 2 076 422 A | 12/1981 |
| EP | 0 172 672 A1 | 2/1983 |
| EP | 2 105 189 A | 3/1983 |
| EP | 0 072 046 A1 | 2/1986 |
| EP | 0 322 687 A2 | 7/1989 |
| EP | 0 365 119 A2 | 4/1990 |
| EP | 0 372 777 A2 | 6/1990 |
| EP | 0 379 793 A1 | 6/1990 |
| EP | 0 384 371 A1 | 6/1990 |
| EP | 0 403 301 A2 | 12/1990 |
| EP | 2 235 627 A | 3/1991 |
| EP | 0 455 892 A1 | 11/1991 |
| EP | 0 461 930 A1 | 12/1991 |
| EP | 0 469 725 A1 | 2/1992 |
| EP | 0 504 112 A2 | 9/1992 |
| EP | 0 518 600 A1 | 12/1992 |
| EP | 0 518 601 A1 | 12/1992 |
| EP | 0 542 314 A1 | 5/1993 |
| EP | 0 628 331 A1 | 12/1994 |
| EP | 0 655 237 A1 | 5/1995 |
| EP | 0 656 206 A1 | 6/1995 |
| EP | 0 656 207 A1 | 6/1995 |
| EP | 0 661 091 A1 | 7/1995 |
| EP | 0 677 332 A2 | 10/1995 |
| EP | 0 681 843 A2 | 11/1995 |

(56) References Cited

FOREIGN PATENT DOCUMENTS

| | | |
|---|---|---|
| EP | 0 709 065 A1 | 6/1996 |
| EP | 2 322 326 A | 8/1998 |
| EP | 0 865 789 A2 | 9/1998 |
| EP | 1 004 349 A1 | 5/2000 |
| EP | 1 022 020 A2 | 7/2000 |
| EP | 1 092 430 B1 | 4/2001 |
| EP | 1 242 013 A2 | 5/2010 |
| EP | 2 258 368 A2 | 12/2010 |
| EP | 0 512 693 A1 | 11/2012 |
| GB | 8 37465 A | 6/1960 |
| GB | 1 429 184 A | 3/1976 |
| GB | 2 001 334 A | 1/1979 |
| GB | 2 371 501 A | 7/2002 |
| JP | 60-227805 A | 11/1985 |
| JP | 1-176437 A | 7/1989 |
| JP | 5-280282 A | 10/1993 |
| SE | 437 766 B | 3/1985 |
| WO | 81/02975 A1 | 10/1981 |
| WO | 86/03750 A1 | 7/1986 |
| WO | 86/04233 A1 | 7/1986 |
| WO | 90/03782 A2 | 4/1990 |
| WO | 90/07333 A1 | 7/1990 |
| WO | 90/09780 A1 | 9/1990 |
| WO | 90/11754 A1 | 10/1990 |
| WO | 91/02645 A1 | 3/1991 |
| WO | 91/04011 A1 | 4/1991 |
| WO | 91/11173 A1 | 8/1991 |
| WO | 91/11179 A1 | 8/1991 |
| WO | 91/11495 A1 | 8/1991 |
| WO | 91/11496 A1 | 8/1991 |
| WO | 91/14422 A1 | 10/1991 |
| WO | 92/00061 A1 | 1/1992 |
| WO | 92/00062 A1 | 1/1992 |
| WO | 92/00107 A1 | 1/1992 |
| WO | 92/06675 A1 | 4/1992 |
| WO | 92/08446 A1 | 5/1992 |
| WO | 92/08447 A1 | 5/1992 |
| WO | 92/11190 A2 | 7/1992 |
| WO | 92/22286 A1 | 12/1992 |
| WO | 92/22287 A1 | 12/1992 |
| WO | 92/22288 A1 | 12/1992 |
| WO | 93/05765 A1 | 4/1993 |
| WO | 93/11743 A1 | 6/1993 |
| WO | 93/11744 A1 | 6/1993 |
| WO | 93/11745 A1 | 6/1993 |
| WO | 93/11747 A1 | 6/1993 |
| WO | 94/03153 A1 | 2/1994 |
| WO | 94/07514 A1 | 4/1994 |
| WO | 94/20204 A1 | 9/1994 |
| WO | 94/22445 | 10/1994 |
| WO | 95/00127 A1 | 1/1995 |
| WO | 95/01221 A1 | 1/1995 |
| WO | 95/01234 A1 | 1/1995 |
| WO | 95/21688 A1 | 8/1995 |
| WO | 95/31479 A1 | 11/1995 |
| WO | 96/00610 A1 | 1/1996 |
| WO | 97/14407 A1 | 4/1997 |
| WO | 97/31691 A1 | 9/1997 |
| WO | 97/36574 A1 | 10/1997 |
| WO | 98/13136 A1 | 4/1998 |
| WO | 98/14179 A1 | 4/1998 |
| WO | 98/17676 A1 | 4/1998 |
| WO | 98/36625 A1 | 6/1998 |
| WO | 98/46215 A1 | 10/1998 |
| WO | 98/52542 A1 | 11/1998 |
| WO | 98/52544 A1 | 11/1998 |
| WO | 99/17742 | 4/1999 |
| WO | 99/44733 A1 | 9/1999 |
| WO | 99/52507 A1 | 10/1999 |
| WO | 99/52550 A1 | 10/1999 |
| WO | 99/55319 A1 | 11/1999 |
| WO | 99/59710 A1 | 11/1999 |
| WO | 99/64014 A1 | 12/1999 |
| WO | 99/66903 | 12/1999 |
| WO | 00/06121 A1 | 2/2000 |
| WO | 00/030612 A1 | 6/2000 |
| WO | 00/030613 A1 | 6/2000 |
| WO | 00/030617 A1 | 6/2000 |
| WO | 00/57851 A1 | 10/2000 |
| WO | 00/067892 | 11/2000 |
| WO | 01/03821 A1 | 1/2001 |
| WO | 01/15664 A1 | 3/2001 |
| WO | 01/067278 A1 | 11/2001 |
| WO | 02/006675 | 1/2002 |
| WO | 02/008447 | 1/2002 |
| WO | 02/019213 | 3/2002 |
| WO | 02/0362462 A1 | 4/2002 |
| WO | 02/038127 | 5/2002 |
| WO | 02/058674 | 8/2002 |
| WO | 02/078675 | 10/2002 |
| WO | 03/008082 A1 | 1/2003 |
| WO | 03/070225 A1 | 8/2003 |
| WO | 03/070226 A1 | 8/2003 |
| WO | 03/074029 A1 | 9/2003 |
| WO | 2004/062784 A1 | 7/2004 |
| WO | 2004062785 A1 | 7/2004 |
| WO | 2004098561 | 11/2004 |
| WO | 2005025506 A2 | 3/2005 |
| WO | 2006/103407 | 10/2006 |
| WO | 2007/011989 | 1/2007 |

OTHER PUBLICATIONS

Lipton, R.B. (1997). "Ergotamine Tartrate and Dihydroergotamine Mesylate: Safety Profiles," Headache 37(1): S33-S41.

Mathew, N.T. (Jan. 1997). "Dosing and Administration of Ergotamine Tartrate and Dihydroergotamine," Headache 37(1):S26-S32.

Saper, J.R. et al (Nov. 2006). "Pharmacology of Dihydroargotamine and Evidence for Efficacy and Safety in Migraine," Headache 48(4): S171-S181.

Schran, H.F. et al. (Jul. 1, 1983) "The Pharmacokinetics and Bioavailability of Subcutaneously Administered Dihydroangotamine, Heparin and the Dihydroergotarnine-Hepartn Combination," Thrombosis Research 31(1): 51-67.

U.S. Appl. No. 11/717,276, filed Mar. 13, 2007, for prosecution from Oct. 16, 2012, through Jul. 30, 2013.

U.S. Appl. No. 12/548,304, filed Aug. 26, 2009, for prosecution from Oct. 6, 2012, through Oct. 18, 2012.

U.S. Appl. No. 12/684,395, filed Sep. 3, 2009, for prosecution from Oct. 31, 2011, through Oct. 10, 2013.

U.S. Appl. No. 12/592,287, filed Nov. 19, 2009, for prosecution from Oct. 5, 2012, through May 15, 2013.

U.S. Appl. No. 12/823,981, filed Jun. 25, 2010, for prosecution from Apr. 17, 2012, through May 15, 2013.

Anonymous. (2000). "The Headaches," Olesen, J. at al. eds., 2nd edition. Lippincott Mama & Wilkins, Philadelphia PA, 10 pages. (Table of Contents Only).

Anonymous. (2004). "Migraine" Part 1 in The International Classification of Headache Disorders 2nd Edition, Cephalaigla 24(Suppl) 9-160. (Table of Contents Only).

Bigal, M.E. et al. (Jul. 25, 2008). "Age-Dependent Prevalence and Clinical Features of Migraine". Neurology 67(2) 248-251.

Crawford, et al (Mar. 2009). "Menstrual time in Adolescents," Headache Mar. 2009, 49(3), pp. 341-347, Epub Feb. 11, 2009.

Lipton, R.B. et al. (Jun. 1993). "Migraine in the United States: A Review of Epidemiology and Health Care Use," Neurology 43(6)(Suppl 3):S6-S10.

Rasmussen, B.K. et al. (Aug. 1992). "Migraine with Aura and Migraine without Aura: An Epidemiological Study," Cephalalgia 12(4):221-228.

Shrewsbury, S. et al, (Mar. 2008, e-pub. Dec. 28, 2007). "Safety and Pharmacokinetics of Diyhdroergotamine Mesylate Administered Via a Novel (Tempo™) Inhaler," Headache 48(3):355-387.

Steiner, T.J. et al. (2003). "The Prevalence and Disability Burden of Adult Migraine in England and Their Relationships to Age, Gender and Ethnicity," Cephalalgia 23(7):519-527.

International Search Report and Written Opinion dated Aug. 30, 2010, for PCT Patent Application No. PCT/US2010/040048, filed on Jun. 25, 2010, 7 pages.

(56) References Cited

OTHER PUBLICATIONS

Al-Omran, M.F. et al. (Oct. 2002). "Formulation and Physicochemical Evaluation of Diclofenac Sodium Chewable Tablets." Saud Pharmaceutical Journal 10(4) 177-183.

Anonymous (Feb. 1991). "International Headache Society Committee on Clinical Trials in Migraine: Guideline for Controlled Clinical Tilde of Drugs in Migraine," Cephalalgia 11(1)1-12.

Barj, M. et al. (Apd115, 1992). "Submicronic MgA12O4 PovRier Synthesis in Supercritical Ethanol", J. of Materilas Sci. 27(8):2187-2192.

Becker, W.J. et al (Mar. 1996). "Effectiveness of Subcutaneous Dihydroargotamine by Home Injection for Migraine", Headache 36(3): 144-148.

Berge, S.M. et al. (1977). "Pharmaceutical Salts" J. Pharm. Sci. 66(1):1-19.

Belgrade, M.J. at al. (Apr. 1989). Comparsion of Single-Dorm Meperidine, Butorphanol, and Dithydroergotemine in the Treatment of Vascular Headache, Neurelogy (39)4:590-592.

Bleich, J. et al (Aug. 15, 1993). "Aerosol Solvent Extraction System—A New Microparticle Production Technique," Pharm.

Bodmeier, R. at al. (Aug. 1995). "Polymeric Microspheres Prepared by Spraying Into Compressed Carbon Mord*" Pharm. Res. 12(8):1211-1217.

Bradford, M. M. (1978). "A Rapid and Sensitive Method for the Quantitation of Micrograsm Quantities of Protein Utilizing the Principle of Protein-Dye Binding," Analytical Biochemistry 72:248-264.

Chang, C.J. at al. (May/Jun. 1991). "Separation of β-Carotene Mixtures Precipitated from Liquid Solvents with High-Pressure CO2:," Biotechnol. Prog. 7(3):275-278.

Chapman, K.R. et el (2008). Inhaler choice in primary practice Eur. Respir. Rev. 14(96):117-122.

Chen, C-K. et al. (Feb. 1994). "Supercritical Antisolvent Fractionation of Polyethylene Simulated with Multistage Algorithm and SAFT Equation of State: Staging Leads to High Selectivity Enhancements for Light Fractions," Ind. Eng. Er. Chem. Res 33(2):306-310.

Chhor, K. et al (1992). "Syntheses of Submtcron TIO2 Powders to Vapor, liquid and Supercritical Phases, a Comparative Study," Materials Chemistry and Physics 32249-264.

Cho, I. J. et al. (2008, epublished Aug. 19, 2008). "The identification of C/EBP6 as a Transcription Factor Necessary for the Induction of MAPK Phosphatese-1 by Toll-Like Receptor-4 Ligland," Archives of Biochemistry and Biophysics 479:88-96.

Colthorpe, P. et al. (Jun. 1992). The Pharmacoldnetics of Pulmonary-Delivered Insulin: A Comparison of Intratracheal and Aerosol Administration to the Rabbit, harmaceutical Research P9(6):764-768.

Cook, R.O. et al. (Apr. 2006). "Delivery Performance Dihydriergotamine Masylate (DHE) Using the Breath Synchronized Plume Controlled Tempo Inhaler™ (BSCPI)," presented at the Respiratory Drug Delivery (RDD x) Conference, Boca Raton, Florida, Apr. 23-27, 2006, located at <http://www.mappharma.com/publications/migriane.htm>, last visited on Aug. 21, 2009,1 page.

Cook, R. et al. (Jul. 2007). "Precision Dosing of Dihydriergotamine (DHE) by Inhalation," presented at the 13th Congress of the International Headache Society, Stockholm, Sweden. Jun. 28, 2007-Jul. 1, 2007, located at Idtp://www.mappharma.com/publications/migraine.htm>, last visited on Aug. 21, 2009,1 page.

Cygnarowicz, M.L. et al. (Jan./Feb. 1990). "Design and Control of a Process to Extract β-Carotene with Supercritical Carbon Dioxide," Biotechnol. Prog. 6(1):82-91.

D'Alesandro, R. et al. (1983). "Menstrual Migraine: Intermittent Prophylaxie With a Timed-Release Pharmacological Formulation of Dihydriergotamine." Cephalalgia Suppl. 1:156-158.

Debenedetti, P.G. et al. (1993) "Application of Supercritical Fluids for the Production of Sustained Delivery Devices," Journal of Controlled Release 2427-44.

Debenedetti, P.G. et al. (1993) "Rapid Expansion of Supercritical Solutions (RESS): Fundamentals and Applications," Fluid Phase Equillibria 82:311-321.

Debenedetti, P.G. et al. (1993) "Supercritical Fluids: A New Medium for the Formation of Particles of Biomedical Interest," Controlled Release of Bioactive Materials, Proceedings of the 20th International Symposium, 20:141-142.

Dixon, D.J. et al. (Jan. 1993). "Polymeric Materials Formed by Precipitation with a Compressed Fluid Antisolvent," AlChE Journal 39(1):127-139.

Donsi, G. et al. (1991). "Micronization by Means of Supercritical Fluids: Possibility of Application to Pharmaceutical Field," Pharm. Aota Helv. 88(5-6).170-173.

Doods, H. et al. (2000). "Pharmacological Profile of BIBN4096Bs, the First Selective Small ,Molecule CGRP Antagonist," British Journal of Pharmacology129(3)420-423.

Edvinsson, L. et el. (1894). Neuropeptides in Migraine and Cluster Headache, Cephalalgia 14:320-327.

Elliott, R.B. et al. (Oct. 1987). Parenteral Absorption of Insulin From the Lung in Diabetic Children, Aust. Paediar. J. 23(5)293-297.

Ferrari, M.D. et al. (1995). 5-HT1 Receptors in Migraine Pathophysiology and Treatment; European Journal of Nourciogy 2:5-21.

Francis, A.W. (Dec. 1954). "Ternary Systems of Liquid Crtbon Dioxide," Journal of Physical Chemistry 58:1099-1114.

Frijns, C.J.M. at el. (2008). "Early Circulating Levels of Endothelial Cell Activation Makers in Aneurysmal Subarachnoid Haemoorrhage: Associations with Combo, Ischaemic Events end Outcome." J. Neural. Psychiatry 77:77-83.

Gallagher, P.M. et al. (1989). "Gas Anfisolvent Recrystallization: New Process to Recrystallize Compounds Insoluble in Supercritical Fluids," Chapter 22 in ACS Symposium Series 406. Supercritical Fluid Science and Technology, Johnston, K.P. et al. eds., American Chemical Society: Washington, DC, pp. 334-354.

Gallagher, P.M. et al. (Jun. 1992). "Gas Anti-Solvent Recrystallization of MX: Formation of Ultra-Fine Particles of a Difficult-to-Communicate Explosive," The Journal of Supercritical Fluids 5(2):130-142.

Gallagher, P.E. ae al. (Nov. 2008, epub. Sep. 3, 2008). "MAP Kinase/Phosphatase Pathway Mediates the Regulation of ACE2 by Anglotensin Peptides," Am. J. Physiol. Cell Physiol. 295:C1189-C1174.

Ghaderi, R. et al (Mar. 2000). "A New Method for Preparing Biodegradable Microparticles and Entrapment of Hydrocortisone in DL-PLG Microparticles Using Supercritical Fluids," European Journal of Pharmaceutical Sciences 10(1)1-9.

Hanoun, N. et al. (2003). "Dihydroergotamine and Its Metabolite, 6'-hydroxy-dihydroergotamine, as 5-HT1A Receptor Agonists in the Rat Brain," British Journal of Pharmacology 139(2):424-434.

Johansson-Haque, K. et al (2008) "Stimulation of MAPK-Phosphates 1 Gene Expression by Glucocorticoids Occurs Through a Tethering Mechanism Involving C/EBP." Journal of Molecular Endocrinology 41:239-249.

Johnson. K.W. et al Serotonin in Migraine: Theories, Animal Models and Emerging Therapies; vol. 51 in Progress in Drug Reesearch, Jucker, E. ed., Birkhäuser Verlag: Basel. Germany. pp. 221-244.

Jeunne. C.L. et el. (1999). "Comparative Efficacy and Safety of Calcium Carbasalate Plus Metoclopramide Verus Ergotamine Tartrate Plus Caffeine in the Treatment of Acute Migraine Attacks," Eur. Neurol. 41:37-43.

Jung, J. et al (2001). Particle Design Using Supercritical Fly Literature and Patent Survey; J. of Supercritical Fluids: Literature and Patent Survey 20:179-219.

Kelman, L. (Oct. 2004). "The Premonitory Symptoms (Prodrome): A Tertiary Care of 893 Migrainueura," Headache 44 885-872.

Klapper, J.A. et al. (Jan. 1992). "Clinical Experience Wth Patient Administered Subcutaneous Dihydroergotamine Mesylate in Refractory Headaches," Headache 32(1):11-23.

Lahiere, R.J. et al (Oct. 1987). "Mass-Transfer Efficiencies of Column Contactors in Supercriticar Extraction Service." Ind. Eng. Chem. Res. 26(10):2086-2092.

Larson. K.A. et al. (Jun. 1986). "Evaluation of Supercritical Fluid Extraction in the Pharmaceutical Industry," Biotechnology Program 2(2):73-82.

(56) References Cited

OTHER PUBLICATIONS

Lee, S-W. et al. (Apr. 1976). "Development of en Aerosol Dosage Form Containing insulin" Journal of Pharmaceutical Sciences 65(4):587-572.

Lipton, R.B. et al. (Jul./Aug. 2001). "Migraine Diagnosis and Treatment: Results From the American Migraine Study II," Headache 41(7):638-645.

Loth, H. et al. (1986). "Properties and Dissolution of Drugs Micronized by Crystallization from Supercritical Gases," International Journal of Pharmaceutics 32:265-267.

Manivet, P. et al. (Mar. 31, 2000). PDZ-Dependent Activation of Nitric-Oxide Syntheses by the Serotonin 2B Receptor, J. Bid Chem. 275(14);9324-9331.

Massiou, H. (1987). Dihydroergotemine Nasal Spray in Prevention and Treatment of Migraine Attacks: Two Controlled Trials Versus Placebo; Cephalagigla pp. 440-441.

Mather, P.J. et al. (Sep. 1991). "The Treatment of Cluster Headaches With Repetitive Intravenous Dihydroergotemine". Headache 31:525-532.

Mathew, N.T. et al. (May 1998). "Coexistence of Migraine and Idiopathic Intracronial Hypertension without Papilledema," Neurology 46:1226-1230.

Matson, D.W. et al. (Jun. 1987). "Production of Powders and Films by the Rapid Expansion of Supercritical Solutions," Journal of Materials Science 22(6):1919-1928.

McCarthy, B.G. et al. (Jul. 1989). "Comparative Neuropharmacology of Dihydroergotamine and Sumatriptan (GR 43175)," Headache 29(7):4420-422.

McGirt, M.J. et al. (Nov. 2002). "Serum Von Williebrand Factor, Matrix Metalloproteinase-9, and Vascular Endothelial Growth Factor Levels Predict the Onset of Cerebral Vascaspasm After Aneurysmal Subarchnoid Hemorrhage", Neurosurgery 51(5):1128-1136.

Meyer, J.D. et al. (Sep. 1998). "Preparation and in vitro Characterization of Gentemycin-Impregnated Biodegradable Beads Suitable for Treatment of Osteomyelitis." Journal of Pharmaceutical Sciences 87(9):1149-1154.

Mohamed, R.S.. et al. (1989). "Solids Formation After the Expansion of Supercritical Mixtures" Chapter 23 in ACS Symposium Series 406. Supercritical Fluid Science and Technology, Johnson, K.P. et al. eds. American Chemical Society: Washington, DC, pp. 355-378.

Moskowitz ,M.A. (Aug. 1992). "Neurogenic Versus Vascular Mechanisms of Sumatriptan and Ergot Alkaloids in Migraine," Trends Pharamcol. Sci. 13(8):307-311.

Nagai, T. et al. (1984). "Powder Dosage Form of Insulin for Nasal Administration," Journal of Controlled Release 1:15-22.

Olesen. J. et al. (May 1994). "Nitric Oxide is a Key Molecule in Migraine and Other Vascular Headaches," Trends Pharmacol. Sci. 15(5):149-153.

Phillips, E.M. et al. (Jun. 21, 1993). "Rapid Expulsion from Stupercritical Solutions: Application to Pharmaceutical Processes," Internatrional Journal of Pharmaceutics 94(1-3):1-10.

Pradalier, A. et "al. (2004). The PROMISE Study: PROphylaxis of Migraine with SEglor® (Dihydroergotamine Mesilate) in French Primary Care", CNS Drugs 18(15):1149-1163.

Randolph, T.W. et al. (Jul./Aug. 1993). "Sub-Micrometer-Sized Biodegradable Particles of Poly(L-Lacilc Acid) via the Gas Antisolvent Spray Precipitation Process," Biotechno.. Prog. 9(4):429-435.

Raskin, N.H. (Jul. 1988). Repetitive intravenous Dihydroegotamine as Therapy for Intractable Migraine; Neurology 38(7):995-997.

Raskin, N.H. (Nov. 1990). "Modern Pharmacotherapy of Migraine," Neurol. Clin. 8(4):857-865.

Read, S.J. et al. (1997). "Furosemide Inhibits Regenerative Cortical Spreading Depression in Anasethetized Cats," Cephalalgia 17:826-832.

Rosen, T.D. (Sep. 12, 2000). "Treatment of a Prolonged Migrainous Aura with Intravenous Furosemide," Neurology 55(5):732-733.

Saadah, H.A. (Jan. 1992). "Abortive Headache Therapy With Intramuscular Dihydroegotamine", Headache 32 (1):18-20.

Schaerlinger, B. et al. (Sep. 2003). "Agonist Actions of Dihydroergotamine at 5-HT2b and 5-HT2c Receptors and Their Possible Relevance to Antimigraine Efficacy," British Journal of Pharmacology 140(2):277-284.

Schmuck, K. et al. (May 1090). "Activation of Meningeal 5-HT2b Receptors: An Early Step in the Generation of Migraine Headache?" Eur. 1 Neurosci. 8(5):959-987.

Shrewsbury, S. et al. (Apr. 2008). "Intra-Pulmonary Artery as Compared to Peripheral Venous Dosing of Dihydroegotamine (DHE) in Telemeterized, Awake Dogs," Poster presented at The American Academy of Neurology (AAN) 58th Annual Meeting, San Diego, California, Apr. 1-8, 2006, located at ,http://www.mappharma.com/publications/migraine.htm>, last visited on Aug. 21, 2009, 1 page.

Shrewsbury, S. et al. (Jun. 2007). "Clinical Safety of Inhaled Dihydroergotamine Mesylate via a Novel system (Tiempo™ Inhaler)," Poster presented at The American Headache Society (AHS) 49th Annual Headache Symposium, Chicago, Illinois, Jun. 6-10, 2007, located at ,http://www.mappharma.com/publications/migraine.htm>, last visited on Aug. 21, 2009, 1 page.

Shrewsbury, S. et al. (Jun. 2007). "Comparative Clinical Pharmacokinetics of Parent Drug and Metabolites following Inhaled Dosing with Dihydroergotamine Mesylate via a Novel System (Tiempo™ Inhaler)," Poster presented at The American Headache Society (AHS) 49th Annual Headache Symposium, Chicago, Illinois, Jun. 6-10, 2007, located at ,http://www.mappharma.com/publications/migraine.htm>, last visited on Aug. 21, 2009, 1 page.

Shrewsbury, S. et al. (Jun. 2007). "Rapid and Sustained Clinical Efficacy and Safety of Inhaled Dihydroergotamine Mesylate Via a Novel (Tiempo™ Inhaler)," Poster presented at The American Headache Society (AHS) 49th Annual Headache Symposium, Chicago, Illinois, Jun. 6-10, 2007, located at ,http://www.mappharma.com/publications/migraine.htm>, last visited on Aug. 21, 2009, 1 page.

Shrewsbury, S. et al. (2008, e-pub. May 28, 2008). Intrapulmonary and Intravenous Administrations of Dihydroergotamine Masylate have Similar Cardiovascular Effects in the Conscious Dog, Br. J. Pharmacol,. 154(6):1254-1265.

Shrewsbury, S. et al. (Jul. 2008, e-pub. Jun. 4, 2008). "Randomized, Double-Blind, Placebo-Controlled Study of the Safety, Tolerability, and Pharmacokinetics of MAP0004 (Orally-inhaled DIE) in Adult Asthmatics," Curr. Med. Res. Opin. 24(7):1977-1985.

Silberstein, S.D. et al. (May 1990)."Repetitive Intravenous DHE in the Treatment of Refractory Headache," Headache 30(8):1134-339.

Silberstein, S.D. et al (Feb. 2003). "Ergotamine and Dihydroergotamine: History, Pharmacology, and Efficacy," Headache 43(2):144-166.

Stahl, E. et al. (1983). "Dense Gas Extraction on a Laboratory Scale: A Survey of earns Recent Results," Fluid Phase Equilibria 10:289-278.

Steckel, H. et al. (Oct. 30, 1998). "Metered-Dose Inhaler Formulation of Fluticaeone-17-4-Propionate Micronized with Supercritical Carbon Dioxide Using the Alternative Propellant HFA-227," International Journal of Pharmaceutics 173(1-2):25-33.

Tietjen, G.E. (2000). The Relationship of Migraine and Stroke, Neuroepidemiology 19:13-19.

Tietjen, G.E. (2005). "The Risk of Stroke in Patients with Migraine and Implications for Migraine Management," CNS Drugs 19(8):683-692.

Tom, J.W. et al. (Sep./Oct. 1991). "Formation of BIoerodible Polymeric Microspheres and Microparticles by Rapid Expansion of Supercritical Solutions," Biotechnol. Prog. 7(5):403-411.

Tom, J.W. at al. (1991). "Particle Formation with Supercritical Fluids—A Review," J. Aerosol. Sci. 22(5)555-584.

Tom, J.W. at al. (1993). "Applications of Supercritical Fluids in the Controlled Release of Drugs," Chapter 19 in ACS Symposium Series 514, Supercritical Fluid Engineering Science Foundamentals and Applications, Kiran, E. et al. eds., American Chemical Society: Washington, D.C., pp. 238-257.

Troy, D. et al. eds. (2006). Remington: The Science and Practice of Pharmacy, 21st Ed., Lippincott, Williams, & Wilkins: Philadelphia, PA. pp. xxi-xxii (Table of Contents only).

Welch, K.M.A. (1997). "Pathogenesis of Migraine," Seminars in Neurology 17(4)335-341.

(56) References Cited

OTHER PUBLICATIONS

Winner. P. et al. (Oct. 1993). "Office-Based Treatment of Acute Migraine With Dihydroergotamine Mesylate," Headache 33(9):471-475.
Winner, P. et al. (Feb. 1998). "A Double Blind Study of Subcutaneous Dihydroergotamine vs Subcutaneous Sumatriptan in the Treatment of Acute Migraine," Arch. Neurol. 53:180-184.
Wyss, P.A. et al. (1991). "Pharmacoidnetic investigation of Oral and IV Dihydroergotamine in Healthy Subjects," Eur. J. Clin. Pharmacol. 41(6):597-602.
Yaglom, J. et al. (Jun. 2003). Inactivation of Dual-Specificity Phosphatases Is involved in the Regulation of Extracellular Signal-Regulated Kinase by Heat Shock and Hsp72, Molecular and Cellular Biology 23(11):3813-3824.
Yeo, S-D. et al. (Feb. 5, 1993). "Formation of Micropertkadate Protein Powders Using a Supercritical Fluid Antisolvent," Biotechnology and Bioengineering 41(3):341-348.
Response to Non-Final Office Action dated Feb. 19, 2009, for U.S. Appl. No. 10/413,467, filed Apr. 14, 2003, 23 pages.
Non-Final Office Action dated Nov. 19, 2008, for U.S. Appl. No. 10/413,457, filed Apr. 14, 2003, 13 pages.
Response to Non-Final Office Action dated Jun. 25, 2008, for U.S. Appl. No. 10/413,457, filed Apr. 14, 2003, 20 pages.
Non-Final Office Action dated Mar. 27, 2008, for U.S. Appl. No. 10/413,457, filed Apr. 14, 2003, 8 pages.
Response to Final Office Action dated Feb. 28, 2008, for U.S. Appl. No. 10/413,457, filed Apr. 14, 2003, 19 pages.
Final Office Action dated Nov. 28, 2007, for U.S. Appl. No. 10/413,457, filed Apr. 14, 2003, 12 pages.
Response to Non-Final Office Action dated Sep. 6, 2007, for U.S. Appl. No. 10/413,457, filed Apr. 14, 2003, 14 pages.
Non-Final Office Action dated Mar. 7, 2007, for U.S. Appl. No. 10/413,457, filed Apr. 14, 2003, 9 pages.
Response to Advisory Action and Request for Continued Examination dated Dec. 21, 2006, for U.S. Appl. No. 10/413,457, filed Apr. 14, 2003, 18 pages.
Advisory Action dated Aug. 10, 2006, for U.S. Appl. No. 10/413,457, filed Apr. 14, 2003, 3 pages.
Response to Final Office Action dated Jul. 27, 2006, for U.S. Appl. No. 10/413,457, filed Apr. 14, 2003, 17 pages.
Final Office Action dated Mar. 27, 2006, for U.S. Appl. No. 10/413,457, filed Apr. 14, 2003, 9 pages.
Response to Notice of Non-Compliant and Non-Final Office Action dated Nov. 14, 2005, for U.S. Appl. No. 10/413,457, filed Apr. 14, 2003, 23 pages.
Notice of Non-Compliant or Non-Responsive dated Sep. 16, 2005, for U.S. Appl. No. 10/413,457, filed Apr. 14, 2003, 2 pages.
Response to Non-Final Office Action dated Sep. 16, 2005, for U.S. Appl. No. 10/413,457, filed Apr. 14, 2003, 23 pages.
Non-Final Office Action dated Jun. 17, 2005, for U.S. Appl. No. 10/413,457, filed Apr. 14, 2003, 7 pages.
Non-Final Office Action dated Apr. 29, 2010, for U.S. Appl. No. 12/069,667, filed Feb. 11, 2008, 8 pages.
Non-Final Office Action dated Jun. 11, 2010, for U.S. Appl. No. 11/717,276, filed Mar. 13, 2007, 10 pages.
Non-Final Office Action dated Jul. 21, 2010, for U.S. Appl. No. 12/648,304, filed Aug. 26, 2009, 13 pages.
Non-Final Office Action dated Jul. 22, 2010, for U.S. Appl. No. 12/548,292, filed Aug. 20, 2009, 13 pages.
Non-Final Office Action dated Sep. 1, 2010, for U.S. Appl. No. 10/572,012, filed Oct. 10, 2007, 14 pages.
Response to Non-Final Office Action dated Sep. 29, 2010, for U.S. Appl. No. 12/069,667, filed Feb. 11, 2008, 10 pages.
Non-Final Office Action dated Oct. 7, 2010, for U.S. Appl. No. 12/839,190, filed Jul. 19, 2010, 7 pages.
Supplemental Response to Non-Real Office Action dated Nov. 8, 2010, for U.S. Appl. No. 12/089,687, filed Feb. 11, 2008, 7 pages.
Response to Non-Final Office Action dated Dec. 7, 2010, for U.S. Appl. No. 11/717,276, filed Mar. 13, 2007, 9 pages.
Response to Non-Final Office Action dated Jan. 20, 2011, for U.S. Appl. No. 12/548,304, filed Aug. 28, 2009, 17 pages.
Response to Non-Final Office Action dated Jan. 20, 2011, for U.S. Appl. No. 12/548,292, filed Aug. 28, 2009, 16 pages.
Final Office Action dated Feb. 11, 2011, for U.S. Appl. No. 11/717,276, filed Mar. 13, 2007, 7 pages.
Non-Final Office Action dated Mar. 3, 2011, for U.S. Appl. No. 12/069,687, filed Feb. 11, 2008, 13 pages.
Response to Non-Final Office Action dated Mar. 7, 2011, for U.S. Appl. No. 12/839,190, filed Jul. 19, 2010, 11 pages.
Notice of Allowance dated Mar. 28, 2011, for U.S. Appl. No. 12/548,292, filed Aug. 26, 2009, 7 pages.
Non-Final Office Action dated Mar. 29, 2011, for U.S. Appl. No. 12/692,287, filed Nov. 19, 2009, 18 pages.
Non-Final Office Action dated Apr. 5, 2011, for U.S. Appl. No. 12/648,304, filed Aug. 26, 2009, 28 pages.
Non-Final Office Action dated Apr. 28, 2011, for U.S. Appl. No. 12/839,190, filed Jul. 19, 2010, 14 pages.
Response after Notice of Allowance dated Jun. 2, 2011, for U.S. Appl. No. 12/548,292, filed Aug. 26, 2009, 7 pages.
Notice of Appeal from the Examiner to the Board of Patent Appeals and Interferences mailed on Jun. 8, 2011, for U.S. Appl. No. 11/717,276, filed Mar. 13, 2007,1 page.
Non-Final Office Action dated Aug. 11, 2011, for U.S. Appl. No. 12/584,395, filed Sep. 3, 2009, 21 pages.
Response to Non-Final Office Action dated Aug. 29, 2011, for U.S. Appl. No. 12/592,287, filed Nov. 19, 2009,12 pages.
Response to Non-Final Office Action dated Aug. 29, 2011, for U.S. Appl. No. 12/839,190, filed Jul. 19, 2010, 20 pages.
Response to Non-Final Office Action dated Sep. 6, 2011, for U.S. Appl. No. 12/548,304, filed Aug. 26, 2009, 31 pages.
International Search Report dated Jan. 27, 2006, for PCT Patent Application No. PCT/US04/29832 filed Sep. 10, 2004, two pages.
International Search Report dated Jun. 9, 2008, for PCT Patent Application No. PCT/US2008/001829 filed Feb. 11, 2008, 3 pages.
Written Opinion dated Jun. 9, 2008, for PCT Application No. PCT/US2008/001829, filed Feb. 11, 2008, 3 pages.
International Preliminary Report on Patentability dated Aug. 20, 2009, for PCT Application No. PCT/US2008/001829 filed Feb. 11, 2008, 7 pages.
Final Office Action dated Oct. 6, 2011, for U.S. Appl. No. 12/592,287, filed Nov. 19, 2009, 28 pages.
Final Office Action dated Nov. 3, 2011, for U.S. Appl. No. 12/839,190, filed Jul. 19, 2010, 10 pages.
Non-Final Office Action dated Nov. 3, 2011, for U.S. Appl. No. 12/069,667, filed Feb. 11, 2008, 8 pages.
Final Office Action dated Nov. 8, 2011, for U.S. Appl. No. 12/548,304, filed Aug. 28, 2009, 30 pages.
Response After Non-Final Office Action dated Dec. 12, 2011, for U.S. Appl. No. 12/069,387, filed Feb. 11, 2008, 10 pages.
Response Alter Final Office dated Dec. 12, 2011, for U.S. Appl. No. 12/839,190, filed Jul. 19, 2010, 8 pages.
Notice of Allowance dated Jan. 3, 2012, for U.S. Appl. No. 12/839,190, filed Jul. 19, 2010, 8 pages.
Request for Continued Examination dated Jan. 5, 2012, for U.S. Appl. No. 11/717,276, filed Mar. 13, 2007, 12 pages.
Response to Final Office Action dated Jan. 9, 2012, for U.S. Appl. No. 12/548,304, filed Aug. 26, 2009, 13 pages.
Advisory Action dated Jan. 25, 2012, for U.S. Appl. No. 12/548,304, filed Aug. 26, 2009, 3 pages.
Notice of Appeal dated Mar. 5, 2012, for U.S. Appl. No. 12/548,304, filed Aug. 26, 2009, 1 page.
Notice of Appeal dated Apr. 5, 2012, for U.S. Appl. No. 12/592,287, filed Nov. 19, 2009, 2 pages.
Non-Final Office Action dated Apr. 16, 2012, for U.S. Appl. No. 11/717,278, filed Mar. 13, 2007, 8 pages.
U.S. Appl. No. 12/459,954, filed Jul. 2009, in the name of Robert Cook, 11 pages.
Frijns, C.J.M. et al. (2006), "Endothetial Cell Activation Markers and Delayed Cerebral Ischaemia in Patients with Subarachnoid Haemorrhage," J. Neurol. Neurosurg. Psychiatry 77:863-867.

* cited by examiner

| Pain Relief Timepoints | Placebo | DHE – 0.5 mg (p-value versus placebo) | | DHE – 1.0 mg (p-value versus placebo) | |
|---|---|---|---|---|---|
| 10 minutes | 0% | 32% | (0.019) | 21% | (0.068) |
| 15 minutes | 7% | 46 % | (0.019) | 21% | (0.286) |
| 30 minutes | 14% | 55% | (0.022) | 22 % | (0.577) |
| 2 hours | 33% | 72% | (0.019) | 65% | (0.071) |
| Sustained 24hrs | 13% | 43% | (0.066) | 44 % | (0.060) |

Figure 1

METHOD OF THERAPEUTIC ADMINISTRATION OF DHE TO ENABLE RAPID RELIEF OF MIGRAINE WHILE MINIMIZING SIDE EFFECT PROFILE

CROSS-REFERENCE TO RELATED APPLICATIONS

This application is a continuation of U.S. patent application Ser. No. 14/921,860, filed on Oct. 23, 2015, which is continuation of U.S. patent application Ser. No. 14/514,322, filed on Oct. 14, 2014, which is a continuation of U.S. patent application Ser. No. 13/406,391, filed on Feb. 27, 2012, which is a continuation of U.S. patent application Ser. No. 12/069,667, filed on Feb. 11, 2008, which issued as U.S. Pat. No. 8,148,377 on Apr. 3, 2012, which claims priority to U.S. Provisional Application Ser. No. 60/900,850, filed on Feb. 11, 2007, the entire contents of each of which is hereby incorporated by reference.

TECHNICAL FIELD OF THE INVENTION

The present invention relates to methods for treatment of migraine. In particular, the present invention relates to methods for treatment of migraine and related symptoms while minimizing side-effects, or adverse effects, associated with administration of medications that alleviate migraine symptoms. More specifically, the invention relates to pharmaceutical compositions containing dihydroergotamine (DHE) and methods in which these pharmaceutical compositions are administered to patients for the treatment of migraine headaches without side effects.

BACKGROUND OF THE INVENTION

Migraine is the most common headache causing patients to consult a physician. According to the American Migraine Study II, approximately 28 million people in the United States aged 12 and older (approximately 13 percent of the population) suffer from headaches that fit the medical definition of migraine established by the International Headache Society. This corresponds to one migraine sufferer in every four U.S. households. The percentage of patients whose headaches fit the medical definition of migraine who are being diagnosed has increased compared to a decade ago. A majority of all migraine sufferers (53 percent) characterize their pain as causing either severe impairment or forcing them to retreat to their beds sometimes for days at a time. There have been no dramatic changes in the way physicians approach the treatment of migraine in the past 10 years. (Lipton R B et al., Headache, (2001) 41:638-645, 646-657).

A three-item Identification of Migraine (ID Migraine) clinical decision rule for the diagnosis of migraine has been developed. (Stewart W F et al., Neurology 1994; 44 (6 suppl 4):S17-23.) A migraine is a type of primary headache that some people get repeatedly over time. Migraines are different from other headaches because they occur with symptoms such as nausea, vomiting, or sensitivity to light. In most people, a throbbing pain is felt only on one side of the head. Migraines are classified as either "with aura" or "without aura." An aura is a group of neurological symptoms, usually vision disturbances that serve as warning sign. Patients who get auras typically see a flash of brightly colored or blinking lights shortly before the headache pain begins. However, most people with migraines do not have such warning signs.

Multiple humoral agents have been postulated as being the major factor in migraine. These include serotonin, histamine, prostaglandins, platelet factors, endorphins, and vasoactive neuropeptides. The etiology of migraine has been studied by many investigators. Present research no longer fully supports the vasodilator/vasoconstrictor mechanism of vascular headache, i.e., arterial dilation causes pain and constriction equals relief. Research also has now implicated a sterile inflammation, possibly occurring in the dura mater, as the causative factor for vascular head pain. An unknown trigger activates perivascular trigeminal axons, which release vasoactive neuropeptides (substance P, calcitonin gene-related peptide, etc.). These agents produce the local inflammation i.e., vasodilation, plasma extravasation, mast cell degranulation which cause transmission of impulses to the brain stem and higher centers which in turn register as head pain (Moskowitz, M. A. (1992) Neurogenic versus vascular mechanisms of sumatriptan and ergot alkaloids in migraine. Trends Pharmacol. Sci. 13, 307-311).

Migraine therapy is either prophylactic or symptomatic. Prophylactic medication may be selected for a patient having two to four or more headaches per month, if they are severe enough to interfere with daily activities. Beta blockers such as propranolol (INDERAL®) are the most commonly used. Other medications frequently used include serotonin antagonists such as methysergide maleate (SANSERT®), calcium channel blockers (VERAPAMIL®), amitriptyline (ELAVIL®), and ergotamine preparations with belladonna alkaloids and phenobarbital. All of these medications have significant side effects including sedation, loss of energy and drive, dry mouth, constipation, weight gain, and gastrointestinal cramping and distress. For symptomatic treatment, ergotamine with caffeine) (CAFERGOT®) is commonly used. Other medications employed for treating migraine include isometheptene mucate) (MIDRIN®, nonsteroidal anti-inflammatory drugs (NSAID's such as MOTRIN®, NAPROXEN®, etc.), dihydroergotamine and the newer triptans, such as sumatriptan) (IMITREX®, etc. When narcotics, such as FIORINAL WITH CODEINE® (butalbital with codeine) are used frequently, additional hazards, including the considerable potential for rebound headaches and habituation are encountered.

The administration of serotonin agonists is well established for the treatment of migraine headache. The serotonin agonists most widely used are the triptans, including sumatriptan, zolmitriptan, naratriptan, rizatriptan, eletriptan, frovatriptan and almotriptan. These compounds bind specifically to serotonin $5-HT_{1D/1B}$ receptors. To a lesser degree, ergot alkaloids such as ergotamine tartrate (referred to herein as ergotamine) and dihydroergotamine mesylate (also referred to as dihydroergotamine or DHE) are also used to a variety of disease states, including, but not limited to the treatment of acute migraine.

Ergotamine and DHE have very low rectal, oral, sublingual and intranasal bioavailability (only 2% to 10% of the administered dose reaches the systemic circulation). These administration routes also result in relatively slow onset of therapeutic efficacy, ranging from 45 minutes for intranasal to 2 hours for oral or sublingual delivery. IV administration has high bioavailability and onset of therapeutic efficacy, usually much less than 30 minutes. However, injections are painful, cause local inflammation, reduce compliance, and because administration by IV requires costly clinical supervision, it would be very desirable to administer the ergot alkaloids by pulmonary inhalation. Pulmonary inhalation of the ergot alkaloids would minimize metabolism before the drugs can reach the circulation because there is rapid transport from the alveolar epithelium into the capillary circulation and because of the relative absence of mechanisms for metabolism in the lungs. Pulmonary delivery has been demonstrated to result in up to 92% bioavailability in the case of ergotamine tartrate. Pulmonary inhalation administration would also avoid gastrointestinal intolerance typical of migraine medications and minimize the undesirable taste experienced with nasal and sublingual administration due to the bitterness of the ergot alkaloids. Pulmonary inhalation would minimize the reluctance to administer treatment associated with the invasiveness of injection and the cost of clinical supervision. Pulmonary inhalation also would allow for rapid relief from the migraine symptoms, as it would deliver the drug to the systemic circulation as fast as an IV bolus, less than 30 minutes, without the invasive nature of injection.

Dihydroergotamine (DHE) was identified as an effective treatment for migraine nearly fifty years ago (Raskin, Neurology 36:995 997 (1986); Silberstein, et al., Headache 30:334 339 (1990); Saadah, Headache 32:18 20 (1992); and Winner, Headache 33:471 475 (1993)). Despite numerous references describing aerosol delivery of ergotamine tartrate, also referred to as ergotamine, for pulmonary inhalation, there are few, if any, teachings related to the delivery of DHE via pulmonary inhalation. Delivery of DHE in the same manner as ergotamine tartrate is not easily accomplished because DHE is very difficult to stabilize in any of the above formulations. DHE (D.H.E. 45®-Novartis) has been administered by intramuscular or intravenous (IV) injection for over 50 years (Belgrade, et al., Neurology 39:590 592 (1989); Winner, Headache 33:471 475 (1993)). DHE (MIGRANAL®—Novartis) has been administered by nasal administration for 10 years. DHE is also effective when given subcutaneously (Klapper, et al., Headache 32:21 23 (1992); Winner, et al., Arch. Neurol. 53:180 184 (1996); and Becker, et al., Headache 36:144 148 (1996)). However, its administration has been associated with an undesirable side effect profile: nausea, emesis, chest tightness and related cardiovascular effects such as blood pressure instability and arterial constriction, have been reported with its use.

Although effective in the treatment of migraine, DHE administration is often accompanied by side effects such as nausea, vomiting and chest pain (Winner, et al., Arch. Neurol. 53:180 184 (1996)). Other side effects observed from postmarketing experience in patients receiving D.H.E. 45® (dihydroergotamine mesylate) injection, USP, include vasospasm, paraesthesia, hypertension, dizziness, anxiety, dyspnea, headache, flushing, diarrhea, rash, increased sweating, cardiac valvulopathy, and pleural and retroperitoneal fibrosis seen after long-term use of dihydroergotamine. At least one side effect, nausea, occurs more frequently after intravenous administration than after intramuscular or intranasal administration. When given subcutaneously at a concentration of only 1.5 mM, DHE has been reported to cause nausea in nearly 16% of treated patients (Winner, et al., Arch. Neurol. 53: 80 184 (1996)). The currently accepted treatment algorithms for injection or IV use of DHE (see FIGS. 6A-6B) call for the administration of an antiemetic prior to or concurrent with administration of DHE to prevent nausea. Patients with known cardiovascular disease are not qualified to receive DHE treatment.

Notwithstanding these undesirable side effects DHE is still considered the "gold standard" for treatment of severe migraine, cluster headache, chronic daily headache. DHE has a longer duration of action than sumatriptan, so headache recurrence rates are lower with its use. (Winner P, et al. A double blind study of subcutaneous dihydroergotamine versus subcutaneous sumatriptan in the treatment of acute migraine. Arch Neurol (1996) 53:180-184.) Thus, there exists a need for procedures to deliver therapeutically effective amounts of DHE in a time-sensitive manner, without precipitating the side-effects traditionally associated with its administration.

SUMMARY OF THE INVENTION

The invention relates to a method for rapid treatment of a disease or condition in an individual with a compound that (a) binds to one or more first receptors, wherein binding of the compound to the first receptors alleviates the disease or condition, and (b) binds to one or more second receptors, wherein binding of the compound to the second receptors causes a side effect, the method comprising: administering to the individual an amount of the compound at a rate sufficient to develop a circulating plasma concentration level of the compound such that compound acts as an agonist against the first receptor and provides relief from the disease or condition, wherein the circulating plasma concentration level of the compound remains below a level necessary for binding to the second receptor to cause a side effect.

In one embodiment, the invention relates to a method for rapid treatment of migraine with DHE, while minimizing side effects, the method comprising: dampening the peak plasma concentration ($C_{max}$) and slightly delaying the peak such as to avoid saturating the dopaminergic and adrenergic receptors, while achieving sufficient binding to the serotonin receptors to alleviate migraine symptoms within a timeframe that permits rapid resolution of migraine symptoms.

In one embodiment, the invention relates to a method for administering DHE or salts, hydrates, polymorphs, prodrugs, ion pairs and metabolites thereof, to a patient in need thereof, an amount of DHE sufficient to reduce a migraine symptom within a 2 hour period, without inducing side-effects.

The invention relates to methods for providing an amount of DHE to an individual sufficient to develop a circulating plasma concentration level of DHE effective for DHE to act as an agonist against a serotonin receptor related to alleviating a migraine symptoms, while insufficient for active binding to an adrenergic or dopaminergic receptor related to nausea and other side effects.

In some embodiments, DHE displays reduced (<50%) or absence of (<20%) active binding at dopaminergic receptors such as $D_2$. In some embodiments, DHE displays absence of (<20%) active binding at 5-$HT_3$ receptors. In some embodiments, DHE displays reduced (<60%) or absence of (<20%) active binding at adrenergic receptors.

In one embodiment, the DHE is administered by any method at a rate such that the $C_{max}$ is less than 40,000 pg/ml concentration in the circulating plasma in humans, and the time following administration when the peak plasma concentration is attained ($T_{max}$) occurs within 30 minutes after administration.

In some embodiments, $C_{max}$ of DHE is less than 20,000 pg/mL, or less than 15,000 pg/mL, or less than 10,000 pg/mL, or less than 7,500 pg/mL in the circulating plasma. In some embodiments, $T_{max}$ of DHE is preferably less than 20 minutes, and most preferably 15 minutes in the circulating plasma.

According to one aspect of the invention the $C_{max}$ of DHE administered by a method of the invention is at least 5-fold, 10-fold or 15-fold reduced from the $C_{max}$ of DHE administered by direct or slow bolus intravenous delivery.

According to one aspect of the invention the $T_{max}$ of DHE administered by a method of the invention is at least 1 minute delayed from the $T_{max}$ of DHE administered by direct intravenous delivery, and the AUC (or area of the curve of the concentration of the drug in the systemic circulation versus time) of the drug delivered by the method of the invention is within 75% of the comparable IV delivered dose.

According to one aspect of the invention the DHE formulation is administered to an individual by a breath activated metered dose inhaler, wherein the DHE is administered at a rate such that the peak plasma concentration ($C_{max}$) is less than 10,000 pg/ml concentration in the circulating plasma in humans, and the time ($T_{max}$) following administration when the peak plasma concentration is attained, is less than 20 minutes after administration, and further wherein the DHE formulation is administered without administering an anti-emetic to the individual.

According to the methods of the invention, administration of DHE to achieve $C_{max}$ and $T_{max}$ as described above, results in at least partial relief from a migraine syndrome including but not limited to pain, nausea, phonophobia and photophobia, within 30 minutes and sustained relief for 24 hours, but does not result in drug induced nausea, cardiovascular side effects or other adverse effects.

According to one embodiment, the at least partial relief from a migraine syndrome is measured by a drop from a IHS score of greater than "0" for a migraine symptom at the time of administration of DHE, to a score of ≤1 at 30, 60, 90 or 120 minutes following administration.

According to the methods of the invention, administration results in peak plasma concentrations of the primary active metabolites, including but not limited to 8-hydroxy dihydroergotamine, at less than 40,000 pg/ml at $C_{max}$. In some embodiments, $C_{max}$ of the primary metabolites is preferably less than 1,000 pg/mL, more preferably less than 500 pg/mL, and most preferably less than 200 pg/mL in the circulating plasma. In some embodiments, the $T_{max}$ of the primary metabolites is preferably less than 90 minutes, and most preferably 60 minutes in the circulating plasma.

In one aspect of the invention, the method involves administration to the systemic circulation of an unit dose of less than 3.0 mg DHE or salts, hydrates, polymorphs prodrugs, ion pairs and metabolites thereof. In a preferred embodiment, an unit dose of 1.0 mg is administered.

The invention also relates to suitable DHE formulations that achieve the desired delivery profile when administered to an individual.

According to the methods of the invention a DHE formulation may be administered by any mode, including but not limited to, intravenous, intra-arterial, intraperitoneal, intrapulmonary, oral, sublingual, buccal, intranasal, oral inhalation, intravesicular, intramuscular, intra-tracheal, subcutaneous, iontophoresis, transdermal, intraocular, intrathecal, transmucosal, and transdermal delivery.

In a preferred mode, the method of administration is by pulmonary inhalation using aerosols, dry powder inhalers, nebulizers, vaporizers, pressurized metered dose inhalers (pMDIs) and the like. In a more preferred embodiment a pMDI such as a breath activated metered dose inhaler (for example, TEMPO™ Inhaler from Map Pharmaceuticals, Mountain View, Calif.) is used to administer DHE.

The invention also relates to kits comprising DHE formulations and instructions for use thereof. In a preferred embodiment, an inhaler device is included. In one embodiment of this kit, the inhaler device is loaded with a DHE formulation. In another embodiment the kit comprises one or more unit doses of the DHE formulation. In one embodiment, the inhaler device is a pMDI such as a breath activated metered dose inhaler (TEMPO™ Inhaler).

The invention further relates to an inhaler device comprising one or more unit doses of a DHE formulation wherein each unit dose is administered at a rate such that the peak plasma concentration ($C_{max}$) is less than 10,000 pg/ml concentration in the circulating plasma in humans, and the time ($T_{max}$) following administration when the peak plasma concentration is attained, is less than 30 minutes after administration.

The present invention and other objects, features, and advantages of the present invention will become further apparent in the following Detailed Description of the Invention and the accompanying Figures and embodiments.

BRIEF DESCRIPTION OF THE DRAWINGS

FIG. 1 shows percentage of subjects obtaining relief from pain with DHE versus placebo.

DETAILED DESCRIPTION OF THE INVENTION

Figure 2:
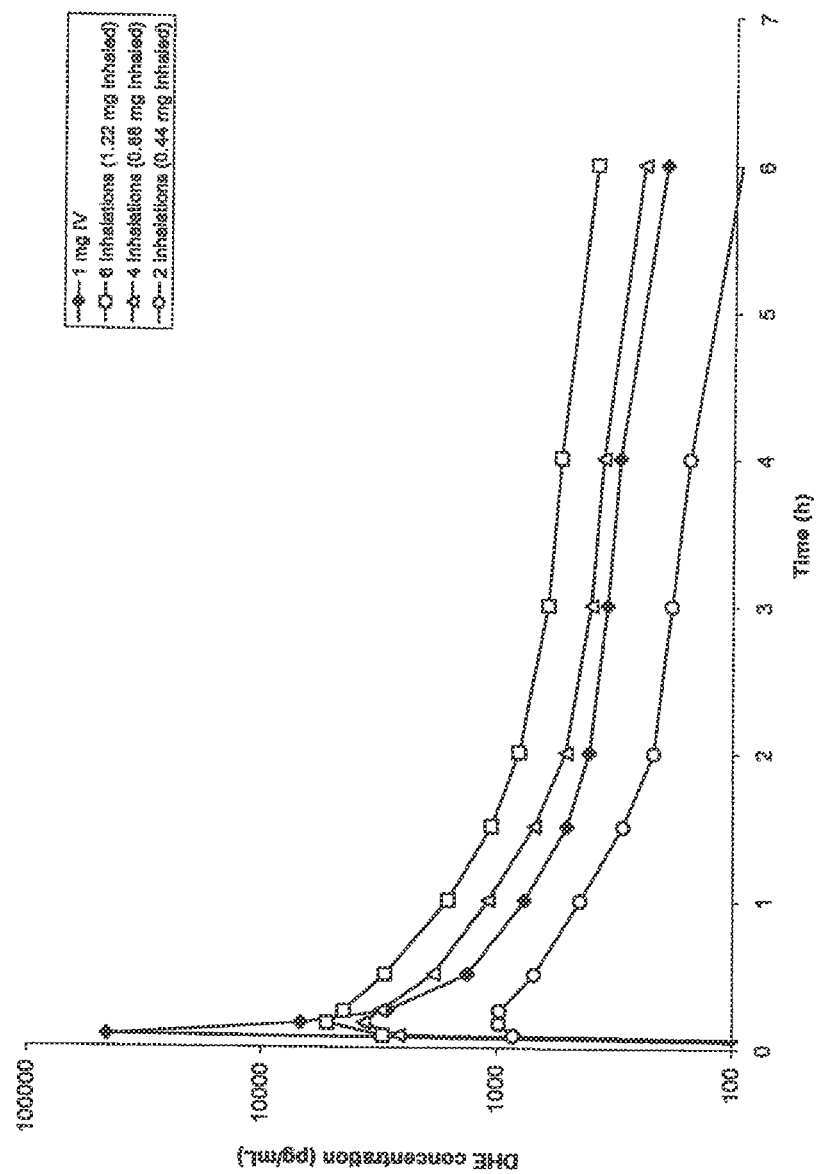
FIG. 2 shows pharmacokinetic profiles for achieving pain relief with minimal side effects.

Use of the term Dihydroergotamine (DHE) according to the methods of invention comprises DHE or salts, hydrates, polymorphs prodrugs, ion pairs and metabolites thereof.

The invention relates to a method for administering DHE or salts, hydrates, polymorphs prodrugs, ion pairs and metabolites thereof, to a patient in need thereof, an amount of DHE sufficient to reduce a migraine symptom within a specified period hour period, without inducing side-effects.

To reduce a migraine symptom within a specified period hour period may involve providing partial relief from at least one migraine syndrome which includes but is not limited to pain, nausea, phonophobia and photophobia, within a period 30, 60, 90, 120 or 180 minutes. Reduction of a migraine symptom further may comprise providing sustained relief for 6, 12, 18, 24 or 36 hours.

Relief from any of the migraine symptoms is measured by a drop from a IHS score of greater than "0" (score of >1 for pain) at the time of administration of DHE, to a score of ≤1 at 30, 60, 90, 120 or 180 minutes following administration. However, freedom from pain (or other severe symptoms) require a reduction in grading of that symptom from an initial >0 result (score of >1 for pain) to 0 at the time point in question.

To reduce a migraine symptom without inducing side-effects may involve administration of therapeutically effective amounts of DHE not resulting in drug induced nausea, emesis, chest tightness and related cardiovascular effects such as blood pressure instability and arterial constriction, or any other adverse effects known to be associated with treatment of migraine with DHE.

The invention relates to methods for providing an amount of DHE to an individual sufficient to develop a circulating plasma concentration level of DHE effective for DHE to act as an agonist against a serotonin receptor related to alleviating a migraine symptoms, wherein the $C_{max}$ is attained within a time period ($T_{max}$) sufficient for providing partial relief from at least one migraine syndrome including but not limited to pain, nausea, phonophobia and photophobia, within a period 30, 60, 90, 120 or 180 minutes, or providing sustained relief for 6, 12, 18, 24 or 36 hours.

Further, the $C_{max}$ attained within a time period ($T_{max}$) according to administration methods of this invention are insufficient for active binding of DHE to an adrenergic or dopaminergic receptor and causing nausea and other side effects.

When binding of DHE to an adrenergic or dopaminergic receptor is insufficient for causing nausea and other side effects, DHE displays reduced (less than 50%) or absence of (20% or less) binding at dopaminergic receptors such as $D_2$; and DHE displays reduced (less than 60%) or absence of (20% or less) binding at adrenergic receptors.

According to the invention, DHE is administered by any method at a rate such that the $C_{max}$ is less than 5,000, 10,000, 20,000, 30,000, 40,000, 50,000, or 60,000 pg/ml concentration in the circulating plasma in humans, and the time following administration when the peak plasma concentration is attained ($T_{max}$) occurs within 10, 15, 20, 30, 45 or 60 minutes after administration.

According to the methods of the invention, administration results in peak plasma concentrations of the primary active metabolites, including but not limited to 8-hydroxy dihydroergotamine, at less than 5,000, 10,000, 20,000, 30,000, 40,000, 50,000, 60,000, 100,000 or 200,000 pg/ml at $C_{max}$. The $T_{max}$ of the primary metabolites is less than 30, 45, 60, 90, or 120 minutes after administration.

According to one aspect of the invention the $C_{max}$ of DHE administered by a method of the invention is at least 5-fold, 10-fold, or 15-fold reduced from the $C_{max}$ of DHE administered by direct intravenous delivery.

According to one aspect of the invention the $T_{max}$ of DHE administered by a method of the invention is at least 1, 2, 5, 10 or 15 minutes delayed from the $T_{max}$ of DHE administered by direct intravenous delivery, and the AUC (or area the curve of the concentration of the drug in the systemic circulation versus time) of the drug delivered by the method of the invention is within 75% of the comparable IV delivered dose.

In one aspect of the invention, the method involves administration of an unit dose comprising about 0.5, 1.0, 2.0, 3.0 or 5.0 mg DHE or salts, hydrates, polymorphs prodrugs, ion pairs and metabolites thereof.

The invention relates to packaged vials, canisters, ampoules, packs, or patches comprising one or more unit doses of DHE. Unit doses may be formulated and packaged in a manner suitable for administration by intravenous, intra-arterial, intraperitoneal, intrapulmonary, oral, sublingual, buccal, intranasal, oral inhalation, intravesicular, intramuscular, intra-tracheal, subcutaneous, iontophoretic, transdermal delivery. In preferred embodiments, the doses of DHE are packaged in a manner suitable for intravenous delivery or pulmonary inhalation.

The invention also relates to suitable solid, liquid or aerosol formulations of DHE that, when administered to a mammal under appropriate conditions, achieve the desired delivery profile defined by AUC, $C_{max}$ and $T_{max}$ values listed above.

According to the methods of the invention a DHE formulation may be administered by any mode necessary to achieve the desired delivery profile defined by $C_{max}$ and $T_{max}$ values listed above, including but not limited to, by intravenous, intra-arterial, intraperitoneal, intrapulmonary, oral, sublingual, buccal, intranasal, oral inhalation, intravesicular, intramuscular, intra-tracheal, subcutaneous, iontophoretic, transdermal administration.

Typically, the DHE formulation will be distributed, either to clinics, to physicians or to patients, in an administration kit, and the invention provides such a migraine treatment kit. Such kits comprise one or more of an administration device (e.g., syringes and needles, inhalators, etc) and a plurality of unit dosages or a reservoir or cache configured to deliver multiple unit doses of the composition as described above. In one embodiment, the administration device is loaded with a DHE formulation. The kit can additionally comprise a carrier or diluent, a case, and instructions for employing the appropriate administration device. In some embodiments, an inhaler device is included. In one embodiment of this kit, the inhaler device is loaded with a reservoir containing the DHE formulation. In another embodiment the kit comprises one or more unit doses of the DHE formulation. In one embodiment, the inhaler device is a pMDI such as a breath activated metered dose inhaler (TEMPO™ Inhaler).

Dihydroergotamine (DHE) for Treatment of Migraine

Dihydroergotamine (DHE) is a semi-synthetic ergot alkaloid, which has been used in the treatment of migraine since 1946. Due to structural similarities with physiological molecules, DHE has wide ranging pharmacology (Table 1), mediated by effects on biogenic amine receptors—specifically serotonin (5-HT) subtypes, adrenergic (α and β) subtypes and dopaminergic (D) subtypes).

Dihydroergotamine is used extensively to treat cluster migraine, pediatric migraine, status migrainosus and chronic daily headache, formerly referred to as "transformed" migraine. DHE is currently administered orally and intranasally (MIGRANAL®-Novartis, U.S. Pat. No. 5,942,251, EP0865789A3, and BE1006872A). However, DHE is most often administered by intramuscular/subcutaneous injection or by intravenous injection (D.H.E. 45®-Novartis) in a clinical setting. (Raskin N H, Neurol Clin. 1990 November; 8(4):857-65.)

Dihydroergotamine binds with high affinity to $5\text{-HT}_{1D\alpha}$ and $5\text{-HT}_{1D\beta}$ receptors. It also binds with high affinity to serotonin $5\text{-HT}_{2A}$, and $5\text{-HT}_{2C}$ receptors, noradrenaline $\alpha_{2A}$, $\alpha_{2B}$ and $\alpha_1$ receptors, and dopamine $D_{2L}$ and $D_3$ receptors.

The therapeutic activity of dihydroergotamine in migraine is generally attributed to the agonist effect at $5\text{-HT}_{1D}$ receptors. Two current theories have been proposed to explain the efficacy of $5\text{-HT}_{1D}$ receptor agonists in migraine. One theory suggests that activation of $5\text{-HT}_{1D}$ receptors located on intracranial blood vessels, including those on arteriovenous anastomoses, leads to vasoconstriction, which correlates with the relief of migraine headache. The alternative hypothesis suggests that activation of $5\text{-HT}_{1D}$ receptors on sensory nerve endings of the trigeminal system results in the inhibition of pro-inflammatory neuropeptide release. In addition, dihydroergotamine possesses oxytocic properties.

The ergot alkaloids are less selective than the triptans when binding to $5\text{-HT}_{1D}$, $5\text{-HT}_{1A}$, $5\text{-HT}_{2A}$, $5\text{-HT}_{2C}$, noradrenaline☐ $\alpha_{2A}$, $\alpha_{2B}$, and α, dopamine $D_{2L}$ and $D_3$ receptors. In acute migraine therapy, DHE is thought to mediate its effects through $5\text{-HT}_{1B}$ receptors (constriction of intracranial extra-cerebral blood vessels) and 5-HT$_{1D}$ receptors (inhibition of trigeminal neurotransmission).

DHE is known to bind specifically to receptors as shown in Table 1. Table 1 shows affinities of DHE (measured as IC$_{50}$) for specific biogenic amine receptors. Potent activity at 5-HT$_{1B}$ and 5-HT$_{1D}$ receptors and wide ranging receptor-binding activity is observed for DHE. (Silberstein, S. D., McCrory, D. C. Ergotamine and dihydroergotamine: history, pharmacology, and efficacy. Headache (2003) 43:144-166.)

The chemical structure of DHE is shown below:

TABLE 1

Receptor binding activity of Dihydroergotamine mesylate (DHE)

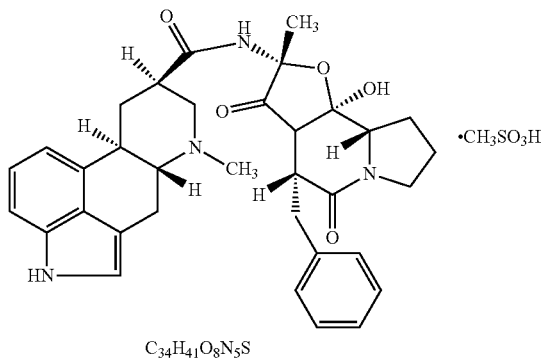

$C_{34}H_{41}O_8N_5S$

| Serotonin Receptor Subtype | Affinity IC$_{50}$ (nM) | Adrenergic Receptor Subtype | Affinity IC$_{50}$ (nM) | Dopaminergic Receptor Subtype | Affinity IC$_{50}$ (nM) |
|---|---|---|---|---|---|
| 1A | 0.4 | α1a | 6.6 | D2 | 1.2 |
| 1B | 0.7 | α1b | 8.3 | D3 | 6.4 |
| 1D | 0.5 | α2a | 1.9 | D4 | 8.7 |
| 1E | 1100 | α2b | 3.3 | | |
| 1F | 180 | α2c | 1.4 | | |
| 2A | 9 | | | | |
| 2C | 1.3 | β1 | 3100 | | |
| 3 | 3700 | β2 | 2700 | | |
| 5 | 60 | β3 | 271 | | |

Formulations and Dosage Forms

A number of studies have been conducted in adults to demonstrate the efficacy and safety of intravenous DHE. The current method of administering intravenous DHE by using repeated intravenous doses of DHE to treat severe migraines was introduced by Raskin (Raskin N H. Repetitive intravenous dihydroergotamine as therapy for intractable migraine. Neurology 1986; 36: 995-997). References to "direct intravenous delivery" in the specification is understood to refer to direct IV administration of DHE according to the procedure set forth in Raskin (Neurology 36: 995-997 (1986)).

Recently, formulations of DHE by itself and in combination with nonsteroidal analgesics have been developed for intramuscular autoinjectors (US 20030040537, U.S. Pat. No. 6,077,539, WO005781A3, EP1165044A2, CN1347313T, and AU0038825A5). DHE in combination with potent analgesics had also been formulated for treatment by intranasal administration (U.S. Pat. No. 5,756,483, EP0689438A1, AU6428894A1, and WO9422445A3). Spray or aerosol formulations have also been developed for the sublingual administration of DHE (US20030017994). Ergotamine tartrate has been administered by injection, rectally with suppositories and via inhalation with metered dose inhaler (MEDIHALER-ERGOTAMINE®; 3M Health Care, Northridge, Calif.), but is most commonly administered orally or sublingually.

There are numerous recent citations of ergotamine tartrate formulations for administration via inhalation (U.S. Pat. No. 6,488,648, U.S. Pat. No. 6,451,287, U.S. Pat. No. 6,395,300, U.S. Pat. No. 6,395,299, U.S. Pat. No. 6,390,291, U.S. Pat. No. 6,315,122, U.S. Pat. No. 6,179,118, U.S. Pat. No. 6,119,853, U.S. Pat. No. 6,406,681) and specifically in propellant based metered dose inhaler (MDI) formulations (U.S. Pat. No. 5,720,940, U.S. Pat. No. 5,683,677, U.S. Pat. No. 5,776,434, U.S. Pat. No. 5,776,573, U.S. Pat. No. 6,153,173, U.S. Pat. No. 6,309,624, U.S. Pat. No. 6,013,245, U.S. Pat. No. 6,200,549, U.S. Pat. No. 6,221,339, U.S. Pat. No. 6,236,747, U.S. Pat. No. 6,251,368, U.S. Pat. No. 6,306,369, U.S. Pat. No. 6,253,762, U.S. Pat. No. 6,149,892, U.S. Pat. No. 6,284,287, U.S. Pat. No. 5,744,123, U.S. Pat. No. 5,916,540, U.S. Pat. No. 5,955,439, U.S. Pat. No. 5,992,306, U.S. Pat. No. 5,849,265, U.S. Pat. No. 5,833,950, U.S. Pat. No. 5,817,293, U.S. Pat. No. 6,143,277, U.S. Pat. No. 6,131,566, U.S. Pat. No. 5,736,124, U.S. Pat. No. 5,696,744). In the late 1980s 3M developed, received approval for and marketed a pulmonary inhalation formulation of an ergotamine tartrate (MEDIHALER-ERGOTAMINE®). It was removed from the market in the 1990s due to difficulties with inconsistent formulation.

Powders for inhalation in dry powder inhalation devices using ergotamine tartrate have also been described (U.S. Pat. No. 6,200,293, U.S. Pat. No. 6,120,613, U.S. Pat. No. 6,183,782, U.S. Pat. No. 6,129,905, U.S. Pat. No. 6,309,623, U.S. Pat. No. 5,619,984, U.S. Pat. No. 4,524,769, U.S. Pat. No. 5,740,793, U.S. Pat. No. 5,875,766, U.S. Pat. No. 6,098,619, U.S. Pat. No. 6,012,454, U.S. Pat. No. 5,972,388, U.S. Pat. No. 5,922,306). An aqueous aerosol ergotamine tartrate formulation for pulmonary administration has also been described (U.S. Pat. No. 5,813,597).

The invention is directed to a pharmaceutical composition in unit dose form containing DHE in an amount such that one or more unit doses are effective in the symptomatic treatment of migraine headache when administered to a patient. The composition may contain excipients. In order to retard the rate of oxidative degradation of the composition, one or more antioxidants may be added. Any salt of DHE may be used but the mesylate salt is preferred. In all cases, formulations may be prepared using methods that are standard in the art (see, e.g., Remington: The Science and Practice of Pharmacy, 21st ed., Lippincott Williams & Wilkins (2005)). In general, patients receive a total dosage of between 0.1 and 10.0 mg, preferably 0.5 to 5.0 mg, or more preferably 1.0-2.0 mg per migraine attack. The dose of the DHE formulation administered to an individual (such as human) will vary with the particular composition and the method of administration, such as to achieve the necessary biogenic amine receptor binding profile required for treating migraine without triggering side effects or adverse effects.

The term "unit dosage form" refers to a physically discrete unit suitable as unitary dosages for an individual, each unit containing a predetermined quantity of active material calculated to produce the desired therapeutic effect, in association with a suitable pharmaceutical carrier, diluent, or excipient. These unit dosage forms can be stored in a suitable packaging in single or multiple unit dosages and may also be further sterilized and sealed.

Also provided are articles of manufacture comprising the compositions described herein in suitable packaging. Suitable packaging for compositions described herein are known in the art, and include, for example, vials (such as sealed vials), canisters with metering valves, vessels, ampoules, bottles, jars, flexible packaging (e.g., sealed Mylar or plastic bags), and the like. These articles of manufacture may further be sterilized and/or sealed.

The compositions may further comprise additional ingredients, for example preservatives, buffers, tonicity agents, antioxidants and stabilizers, nonionic wetting or clarifying agents, viscosity-increasing agents, absorption enhancing agents, and the like.

Suitable absorption enhancement agents include N-acetylcysteine, polyethylene glycols, caffeine, cyclodextrin, glycerol, alkyl saccharides, lipids, lecithin, dimethylsulfoxide, and the like.

Suitable preservatives for use in a solution include polyquaternium-1, benzalkonium chloride, thimerosal, chlorobutanol, methyl paraben, propyl paraben, phenylethyl alcohol, disodium edetate, sorbic acid, benzethonium chloride, and the like. Typically (but not necessarily) such preservatives are employed at a level of from 0.001% to 1.0% by weight.

Suitable buffers include boric acid, sodium and potassium bicarbonate, sodium and potassium borates, sodium and potassium carbonate, sodium acetate, sodium biphosphate and the like, in amounts sufficient to maintain the pH at between about pH 6 and pH 8, and preferably, between about pH 7 and pH 7.5.

Suitable tonicity agents are dextran 40, dextran 70, dextrose, glycerin, potassium chloride, propylene glycol, sodium chloride, and the like, such that the sodium chloride equivalent of the ophthalmic solution is in the range 0.9 plus or minus 0.2%.

Suitable antioxidants and stabilizers include sodium bisulfite, sodium metabisulfite, sodium thiosulfite, thiourea, caffeine, cromoglycate salts, cyclodextrins and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxymethylpropylcellulose, lanolin, methylcellulose, petrolatum, polyethylene glycol, polyvinyl alcohol, polyvinylpyrrolidone, carboxymethylcellulose and the like.

Modes of Administration

The compositions described herein can be administered to an individual (such as human) via various routes, including, for example, intravenous, intra-arterial, intraperitoneal, intrapulmonary, oral, inhalation, intravesicular, intramuscular, intra-tracheal, subcutaneous, intraocular, intrathecal, transmucosal, and transdermal. In one embodiment of the invention, nanoparticles (including protein or carbohydrate nanoparticles, co-formulated with drug) of the inventive compounds can be administered by any acceptable route including, but not limited to, orally, intramuscularly, transdermally, intravenously, through an inhaler or other air borne delivery systems and the like.

When preparing the composition for injection, particularly for intravenous delivery, the continuous phase preferably comprises an aqueous solution of tonicity modifiers, buffered to a pH range of about 4 to about 8.5. The pH may also be below 7 or below 6. In some embodiments, the pH of the composition is no less than about 6, including for example no less than about any of 6.5, 7, or 8 (such as about 7.5 or 8).

In a preferred embodiment the DHE is delivered using inhalation therapy. Many preclinical and clinical studies with inhaled compounds have demonstrated that efficacy can be achieved both within the lungs and systemically. Moreover, there are many advantages associated with pulmonary delivery including rapid onset, the convenience of patient self-administration, the potential for reduced drug side-effects, ease of delivery by inhalation, the elimination of needles, and the like.

Inhalation aerosols from dry powder inhalers, nebulizers, vaporizers and pressurized metered dose inhalers typically include excipients or solvents to increase stability or deliverability of these drugs in an aerosol form. Additionally, the particle size of the drug aerosols may be controlled to provide the uptake characteristics consistent with the methods of the invention. Typically, particle sizes are controlled to desirable sizes known by those skilled in the art. For example, when using dry powder inhalers (DPI's), the drug particles are generated from the bulk drug by attrition processes such as grinding, micronizing, milling, or by multiphase precipitation processes such as spray drying, solution precipitation, supercritical extraction/precipitation or lyophilization to yield powders that can be dispersed in the propellant to obtain an acceptable particle size for delivery to the lungs. As dry powder formulations are prone to aggregation and low flowability which can result in diminished efficiency, scrupulous attention is required during milling, blending, powder flow, filling and even administration to ensure that the dry powder aerosols are reliably delivered and have the proper particle size distribution for delivery to the lungs.

Nebulizers generate an aerosol from a liquid, some by breakup of a liquid jet and some by ultrasonic vibration of the liquid with or without a nozzle. Liquid formulations are prepared and stored under aseptic or sterile conditions since they can harbor microorganisms. The use of preservatives and unit dose packaging is contemplated. Additionally solvents, detergents and other agents are used to stabilize the drug formulation.

Pressurized metered dose inhalers, or pMDIs, are an additional class of aerosol dispensing devices. pMDIs package the compound in a canister under pressure with a solvent and propellant mixture, usually chlorofluorocarbons (CFCs), or hydrofluoroalkanes (HFAs). Upon being dispensed a jet of the mixture is ejected through a valve and nozzle and the propellant "flashes off" leaving an aerosol of the compound. Due to the high speed ejection of the aerosol from the nozzle, some of the drug may impact ballistically on the tongue, mouth and throat and never reach the lung.

While aerosol delivery of ergotamine tartrate for pulmonary inhalation is widely known, delivery of DHE via pulmonary inhalation has been used rarely, as DHE is very difficult to stabilize in formulations suitable for pulmonary delivery. To maintain potency and activity the DHE must be formulated in a solution, powder or suspension that can be stabilized without excipients or with excipients that are not toxic to the lungs. Since DHE is extremely sensitive and will degrade on exposure to light, oxygen, heat and in the presence of many chemical compounds commonly used in medicinal formulations, stabilization is not easily achieved. The current formulations for delivery of DHE by aqueous nasal sprays or by injection require chelating or complexing agents, such as dextran or cyclodextrins, to stabilize the DHE in solution. To preserve the DHE solution from degradation it is sealed in difficult-to-use dark-glass vials that must be opened with a complicated opener and transferred to injector or spray applicator immediately prior to use. Only recently stable formulations for pulmonary delivery of DHE have been described in U.S. application Ser. No. 10/572,012 and WO2005/025506A2.

WO2005/025506A2 describes suitable, stable formulations of dihydroergotamine, or pharmaceutically acceptable salts thereof, to administer dry powders and propellant suspensions via pulmonary aerosol inhalation or nasal spray inhalation. In one embodiment, DHE is used as the mesylate salt. The DHE powder is generated using supercritical fluid processes which offer significant advantages in the production of DHE particles for inhalation delivery and produce respirable particles of the desired size in a single step. The disclosures of U.S. application Ser. No. 10/572,012 and WO2005/025506A2 are incorporated herein by reference in their entirety.

In a preferred embodiment, the inhaled dosing is carried out with a breath actuated inhaler such as the Tempo™ Inhaler (Map Pharmaceuticals, Inc., Mountain View, Calif.). The Tempo™ Inhaler is a pressurized metered-dose inhaler (pMDI) which addresses limitations of standard pMDI inhalers: inconsistent dosing and drug delivery inefficiency. The Tempo Inhaler provides breath actuation, enhancing patient compliance, and efficient, reliable dose-to-dose consistency that is independent of the inhalation flow rate. It achieves these advantages by combining proprietary features such as the breath synchronized trigger and the flow control chamber and dose counter/lockout in a small, easy to use device. These advanced aerodynamic control elements are driven only by the patient's breath, avoiding expensive, power consuming electronics, resulting in an affordable, reliable and disposable platform.

Measuring Efficiency of DHE Administration

The current invention teaches a method of administration of DHE that minimizes or eliminates side effects while at the same time achieving a dosing profile sufficient to provide effective and rapid relief from the four primary symptoms of migraine syndrome: pain, nausea, phonophobia and photophobia. In clinical trials conducted by the inventors, an unanticipated phenomenon was observed. When DHE was administered in the aforementioned manner, a very high "spike" in peak plasma concentration was unexpectedly avoided, the side effects of nausea, chest tightness or pain, blood pressure excursions, emesis could be minimized or completely eliminated while still achieving rapid relief from the migraine symptoms.

Efficacy of a migraine therapy regimen can be evaluated based on primary and secondary endpoints. Primary efficacy endpoint may be a pain-free response rate at about 2 hours post-dose. Secondary efficacy endpoints examine 3 areas of interest: pain-free response at time points earlier than 2 hours post-dose; non-progression of headache; and impact on normal activities.

All four migraine symptoms—pain, nausea, phonophobia and photophobia—are scored at each time point on a four point scale developed by the International Headache Society (IHS; International Headache Society Committee on Clinical Trials in Migraine. Guidelines for controlled clinical trials of drugs in migraine, 1st ed. Cephalalgia 1991; 11:1-12):

0=none
1=mild symptom, not interfering with normal daily activities
2=moderate symptom, causing some restriction to normal activities
3=severe, leading to inability to perform normal daily activities Headache pain intensity is measured on the 4-point severity scale (0=no pain, 1=mild, 2=moderate, 3=severe). The average time to headache improvement (one point below the original intensity), to mild headache, and to no headache is measured. An effective migraine therapy would reduce a headache symptom to mild or non by 1.5 to 2 hours.

Relief from any of the four symptoms require a drop from a score of >0 at time of report of onset of migraine attack (score of >1 for pain), to a score of ≤1 at the time point in question. However, freedom from pain (or other symptom) require a reduction in grading of that symptom from an initial >0 result (score of >1 for pain) to 0 at the timepoint in question.

Functional disability (ability to perform usual daily activities) is measured with a 4 point scale:
0=not at all impaired
1=slightly impaired
2=moderately impaired
3=severely or completely impaired There is a further question (How well did your Study Medication work?) at certain timepoints asking subjects to evaluate the "global effectiveness" of their study medication using a 7 point categorical scale:
0=very much better
1=much better
2=a little better
3=no change
4=a little worse
5=much worse
6=very much worse Mechanisms of Action Investigation of receptor binding at the $C_{max}$ concentrations described in detail in Examples 2 and 3, provided a rationale for the differences observed in the adverse effect profile. Without being bound by theory, it is hypothesized that a method for treating migraine with DHE without triggering side effects can be achieved by controlling the $C_{max}$ concentration to minimize binding to dopaminergic and adrenergic receptors and thus avoiding side effects, while achieving sufficient serotonin receptor binding to be effective in treating migraine symptoms.

Figure 3:
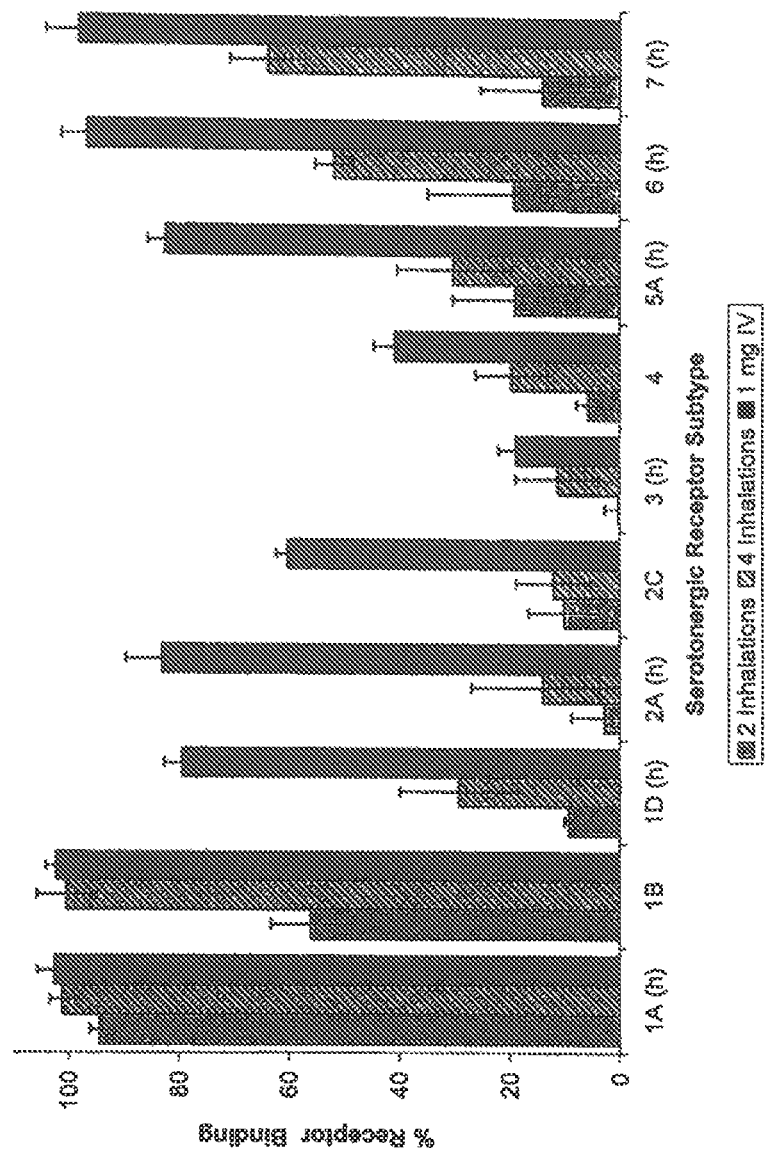
FIG. 3 shows radioligand receptor binding profile for serotonergic receptor subtypes based on dose and administration route. Less than 20% was classed as inactive binding. "(h)" represents cloned human receptor subtypes.

Clinical data (Table 2) show that inhaled dihydroergotamine reduces incidence of nausea compared to intravenous administration (8% vs. 63% respectively). 5-$HT_3$ receptors are known to be implicated in nausea. Antagonists at these receptors, such as ondansetron and granisetron prevent chemotherapy-induced nausea and vomiting. However, a potential agonist role of DHE at 5-$HT_3$ receptors can be ruled out by inactive binding (<20%) for all DHE delivery routes investigated (FIG. 3). Subsequent functional assays also confirmed lack of agonist or antagonist activity at 5-$HT_3$ receptors.

The likely adverse effect profile of DHE is secondary to agonist activity at 5-$HT_{1A}$, 5-$HT_{2A}$, and dopamine $D_2$ receptors. (Silberstein, S. D., McCrory, D. C. Ergotamine and dihydroergotamine: history, pharmacology, and efficacy. Headache (2003) 43:144-166.) The similar levels of 5-$HT_{1A}$ receptor binding for all doses and administration routes rules out this receptor as the cause for the differential adverse effect profile, in particular for dizziness. Indeed, 5-$HT_{1A}$ receptors are believed to play a role in DHE-mediated migraine prophylaxis. (Hanoun, N., et al. Dihydroergotamine and its metabolite, 8-hydroxy-dihydroergotamine, as 5-HT1A receptor agonists in the rat brain. British Journal of Pharmacology 2003; 139:424-434.)

DHE has excitatory actions at vascular α-adrenergic receptors and have agonist activity at constrictor 5-$HT_{2A}$ receptors. These actions underlie peripheral vasoconstrictor effects, in particular on coronary artery smooth muscle. As such, DHE and related ergot compounds are contraindicated in coronary and peripheral vascular disease. It is notable however that $C_{max}$ binding activity was lower for the higher inhaled (14%) vs. intravenous dosing (83%) at 5-$HT_{2A}$ receptors. The effect of other serotonergic subtypes and adrenergic types on the adverse effect profile is not certain. However, binding at $C_{max}$ following intravenous administration yields significantly higher binding (FIGS. 3-5) vs. inhaled $C_{max}$, which may play a role in nausea, in particular for adrenergic blockade.

Both neuronal and vascular mechanisms have been proposed as the basis of actions of 5-HT in migraine. The vasodilatory theory of migraine suggests that extracranial arterial dilation during an attack is related to migraine pain. In the neurogenic dural inflammation theory of migraine, inflammation of the dural membrane surrounding the brain is due to release of neuropeptides from primary sensory nerve terminals. Substance P, calcitonin gene-related peptide and NO all play a role in the dural inflammatory cascade. NO is suspected to play a key role in migraine since NO donors cause a dose-dependent headache with several migrainous characteristics. A cause of migraine could be increased amounts and/or affinity of an enzyme in the NO-triggered cascade of reactions (Olesen et al., Trends Pharmacol. Sci. 1994; 15:149-153).

It has been shown that $5-HT_{2B}$ receptors stimulate the NO production in cell lines (Manivet P., et al., PDZ-dependent activation of nitric-oxide synthases by the serotonin 2B receptor. J. Biol. Chem. 2000; 275:9324-9331) and relaxation of the pig cerebral artery (Schmuck et al., Eur. J. Neurosci. 1996; 8:959-967). Thus, $5-HT_{2B}$ receptors located on endothelial cells of meningeal blood vessels have been proposed to trigger migraine headache through the formation of NO. The long half-life of DHE may account for the low rate of headache recurrence at least partially through permanent inhibition of vascular $5-HT_{2B}$-dependent second messengers (NO) via its major active metabolite 8'-OH-DHE. (Schaerlinger B., et al., British Journal of Pharmacology (2003) 140, 277-284.)

D2 receptor antagonists, i.e. metoclopramide and domperidone, are effective anti-nausea therapies. DHE at IV dose $C_{max}$ levels exhibits 50% receptor binding in D2 assays (FIG. 5) and therefore may result in the clinically reported nausea and dizziness, mediated through agonist activity. Conversely, no binding affinity was reported after inhaled dosing. In addition to data reported here, DHE also has minimal binding activity at muscarinic (M) receptors, and thus rules out chemoreceptor trigger zone M receptor-mediated nausea. (McCarthy, B. G., Peroutka, S. J., Comparative neuropharmacology of dihydroergotamine and sumatriptan (GR 43175). Headache 1989; 29:420-422.)

The receptor-binding studies described in Examples 2 and 3 may explain the unexpected results from the novel method of treating migraine rapidly with DHE, while minimizing side effects. The method dampens the peak plasma concentration ($C_{max}$) and slightly delays the peak so as to avoid saturating the dopaminergic and adrenergic receptors, while achieving sufficient binding to the serotonin receptors to have the desired therapeutic effect of treating migraine.

EXAMPLES

Without further elaboration, it is believed that one skilled in the art can, using the preceding description, utilize the present invention to its fullest extent. The following examples are illustrative only, and not limiting of the remainder of the disclosure in any way whatsoever.

Example 1: Pharmacokinetic Profile of DHE Required to Achieve Pain Relief

FIG. 1 shows the rapid pain relief (within 10 minutes) achieved by administering DHE by a method that achieves the two lower peak plasma concentration profiles shown in FIG. 2.

FIG. 2 shows DHE plasma profiles for 1 mg IV-administered DHE, compared to 6 inhalations (1.22 mg inhaled/fine particle dose), 4 inhalations (0.88 mg inhaled/fine particle dose) and 2 inhalations (0.44 mg inhaled/fine particle dose) of DHE respectively. A large plasma spike was observed following IV DHE administration, but not with inhaled delivery of DHE. This plasma spike difference (of at least "10" fold) was hypothesized to be associated with the reduced side effect profile, despite smaller differences in AUC between 1 mg IV and 0.88 mg inhaled DHE.

Figure 7:
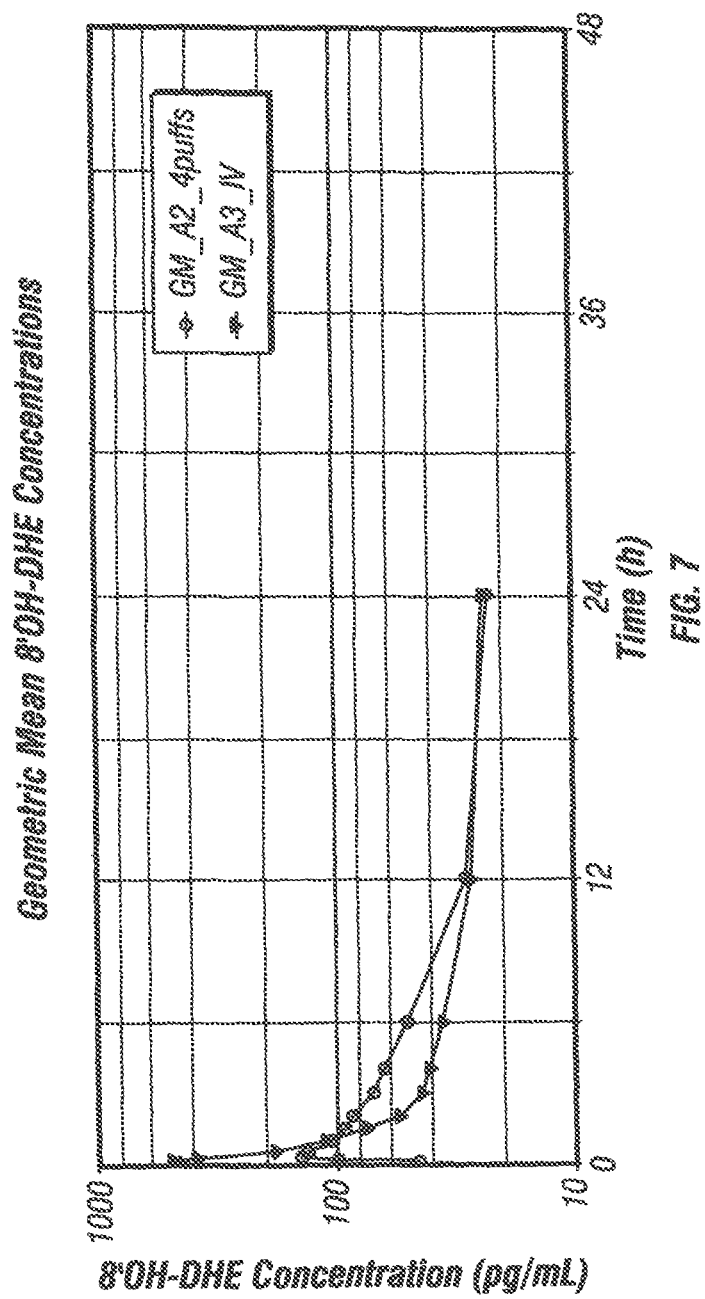
FIG. 7 shows geometric mean 8'OH-DHE concentrations over time following administration of DHE by inhalation and intravenous (IV) routes.

FIG. 7 shows the plasma profile of the primary metabolite of DHE, 8'-OH Dihydroergotamine, following intravenous and inhalation delivery of DHE. A larger plasma spike in 8'-OH Dihydroergotamine was observed following IV DHE administration, but not with inhaled delivery of DHE. This plasma spike difference also is hypothesized to be associated with the reduced side effect profile. The inhalable administration results in a peak plasma concentration of 8-hydroxy-dihydroergotamine of less than 1,000 pg/ml, preferably less than 500 pg/mL, more preferably less than 200 pg/mL at $C_{max}$ in the circulating plasma. The inhalable administration also results in the $T_{max}$ of the primary metabolites (e.g., 8'-OH Dihydroergotamine) to be less than 90 minutes in the circulating plasma.

The inventors have discovered that these slightly delayed, lower peak pharmacokinetic profiles are associated with minimized side effects. The side effects elicited by these administration profiles are shown in the Table 2. The two lower curves, 0.88 mg and 0.44 mg DHE in FIG. 2, achieved therapeutic efficacy within 30 minutes, but elicited only minor side effects with the 0.88 mg dose, and no side effects were observed with the 0.44 mg dose. The highest curve, 1.0 mg IV DHE—the typical therapeutic regimen practiced in clinics today—resulted in significant side effects including nausea and emesis. The observed lower $C_{max}$ or peak plasma concentration difference which was approximately 10 times lower than IV, was theorized to be associated with the observed differential side effect profile, while the smaller differences in AUC, differences of only "1.2" fold, between 1 mg IV and 0.88 mg inhaled enabled therapeutic efficacy. The delivery profiles shown in FIG. 2 were achieved in this instance by inhalation administration, but could also be achieved by infusion pump, nasal, or iontophoretic transdermal or other routes or administration, that were tailored to give a similar slight delay in reaching peak plasma concentrations and a similar damping of peak concentrations, while achieving similar AUCs.

TABLE 2

Side effects associated with the pharmacokinetic profiles in FIG. 2

|  | 1 mg DHE IV, n = 16 (%) | 0.88 mg DHE Inhaled, n = 12 (%) |
|---|---|---|
| Nervous System | | |
| Dizziness | 7 (44) 7r | 1 (8) |
| Paresthesia | 5 (31) 5r | 0 |
| Gastrointestinal System | | |
| Nausea | 10 (63) 10r | 1 (8) |
| Vomiting | 2 (13) 2r | 0 |
| General disorders | | |
| Feeling hot | 3 (19) 3r | 0 | r = considered by investigator related to study drug

Example 2: Receptor Binding at the $C_{max}$ Concentrations

A differential adverse effect profile was reported in a clinical study comparing 1 mg IV-administered DHE with inhaled DHE (Table 2). A greater incidence of adverse effects were apparent following IV dosing. To investigate pharmacologically-mediated adverse effect differences between (1) intravenous and (2) inhaled Dihydroergotamine Mesylate (DHE), biogenic amine receptor binding (serotonin (5-HT), adrenergic, dopaminergic) of dihydroergotamine mesylate in vitro was determined, based on concentrations corresponding to the $C_{max}$ levels reported following inhaled and intravenous (IV) dosing in a clinical study.

To investigate the unexpected result that the lower spikes of DHE may have resulted in a different receptor binding profile thus achieving efficacy, but avoiding side effects, a clinical investigation of receptor binding at the $C_{max}$ concentrations were undertaken.

Peak Plasma DHE concentrations ($C_{max}$) were determined from plasma samples (LC-MS/MS) following intravenous administration (1 mg) by infusion over 3 minutes, and from plasma samples (LC-MS/MS) following inhaled dosing (0.88 mg and 0.44 mg doses), where doses were given by multiple actuations from an inhaler over a period of 2-4 minutes. The inhaled doses represent the expected systemic delivered dose and were estimated from the fine particle dose delivered ex-actuator. The observed $C_{max}$ data is presented in FIG. 2 for DHE. A similar approach was also taken with the primary metabolite, 8'-OH-DHE.

Table 3 presents in vitro concentrations equivalent to $C_{max}$. These concentrations were selected for receptor-binding investigations for both DHE and 8'-OH-DHE.

TABLE 3

Concentrations equivalent to peak plasma concentrations investigated for receptor binding.

| Dose level | Dihydroergotamine Mesylate (pg/mL) | 8'-OH Dihydroergotamine (pg/mL) |
|---|---|---|
| 1 mg IV | 53,215 | 378 |
| 0.88 mg inhaled | 4,287 | 149 |
| 0.44 mg inhaled | 1,345 | 58 |

Figure 4:
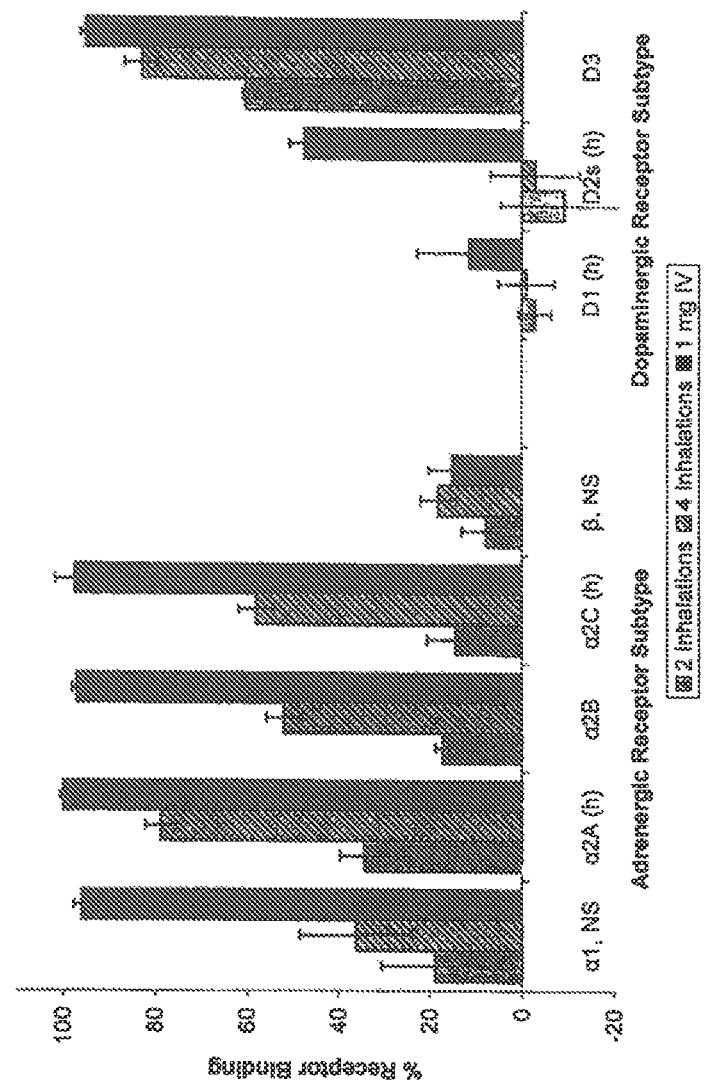
FIG. 4 shows radioligand receptor binding profile for adrenergic and dopaminergic receptor subtypes based on dose and administration route. Less than 20% was classed as inactive binding. "(h)" represents cloned human receptor subtypes and "NS" indicates non-specific binding.
Figure 5:
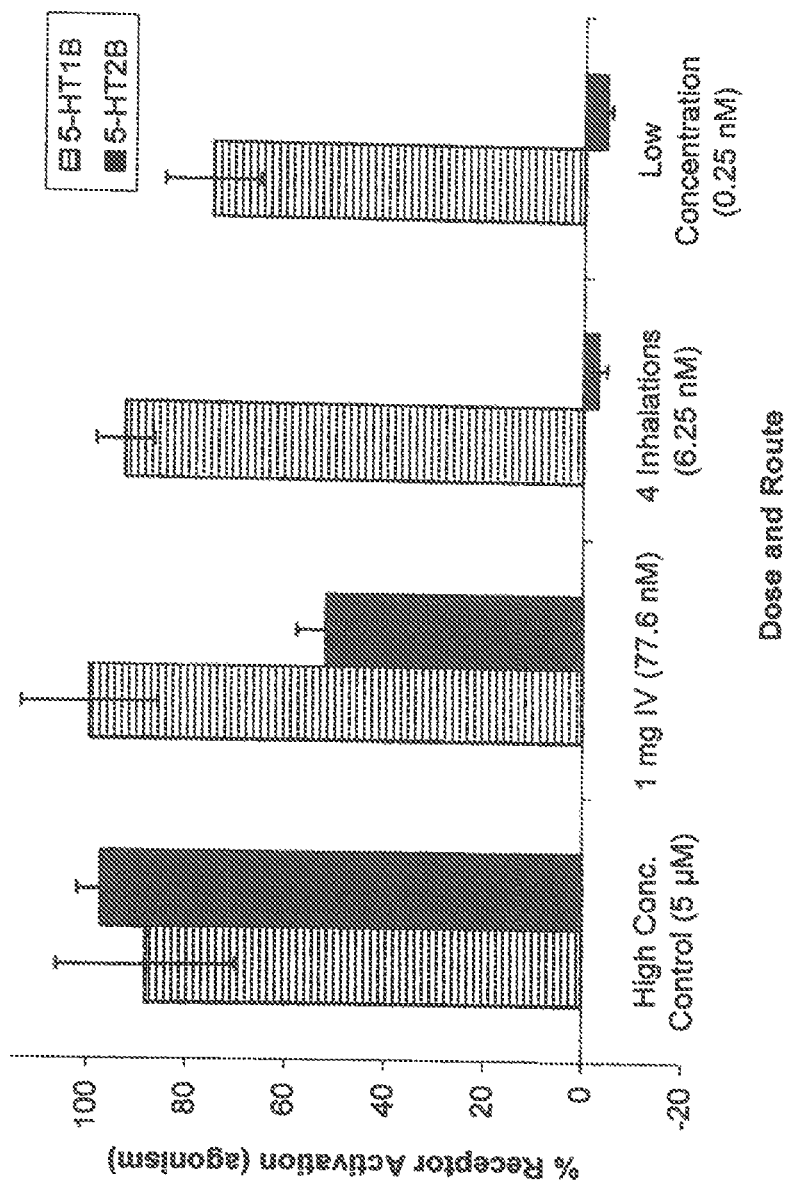
FIG. 5 shows selective agonism at $5\text{-}HT_{1B}$ and $5\text{-}HT_{2B}$ receptors at various concentrations of DHE.
Figure 6A:
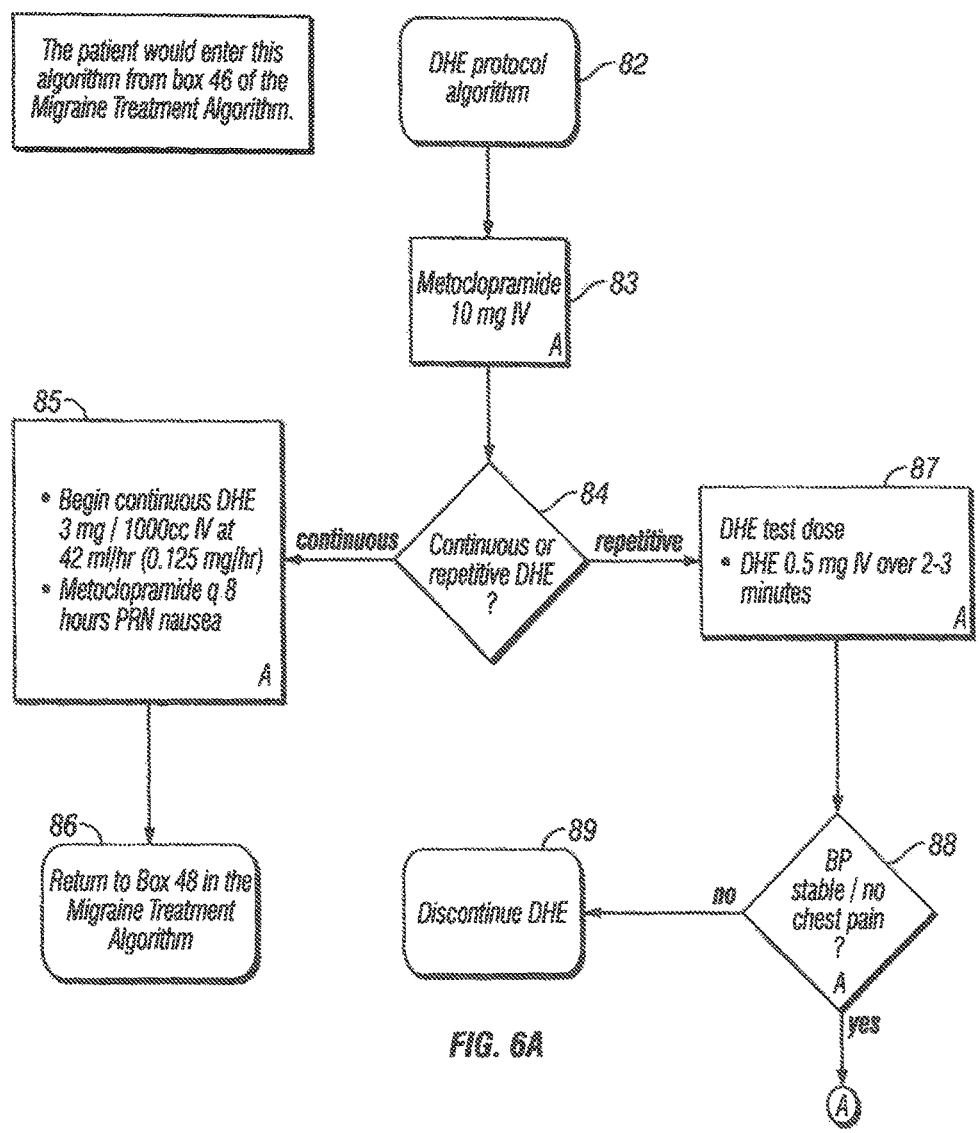
FIG. 6A and FIG. 6B show currently accepted treatment algorithms for injection or IV administration of DHE.
Figure 6B:
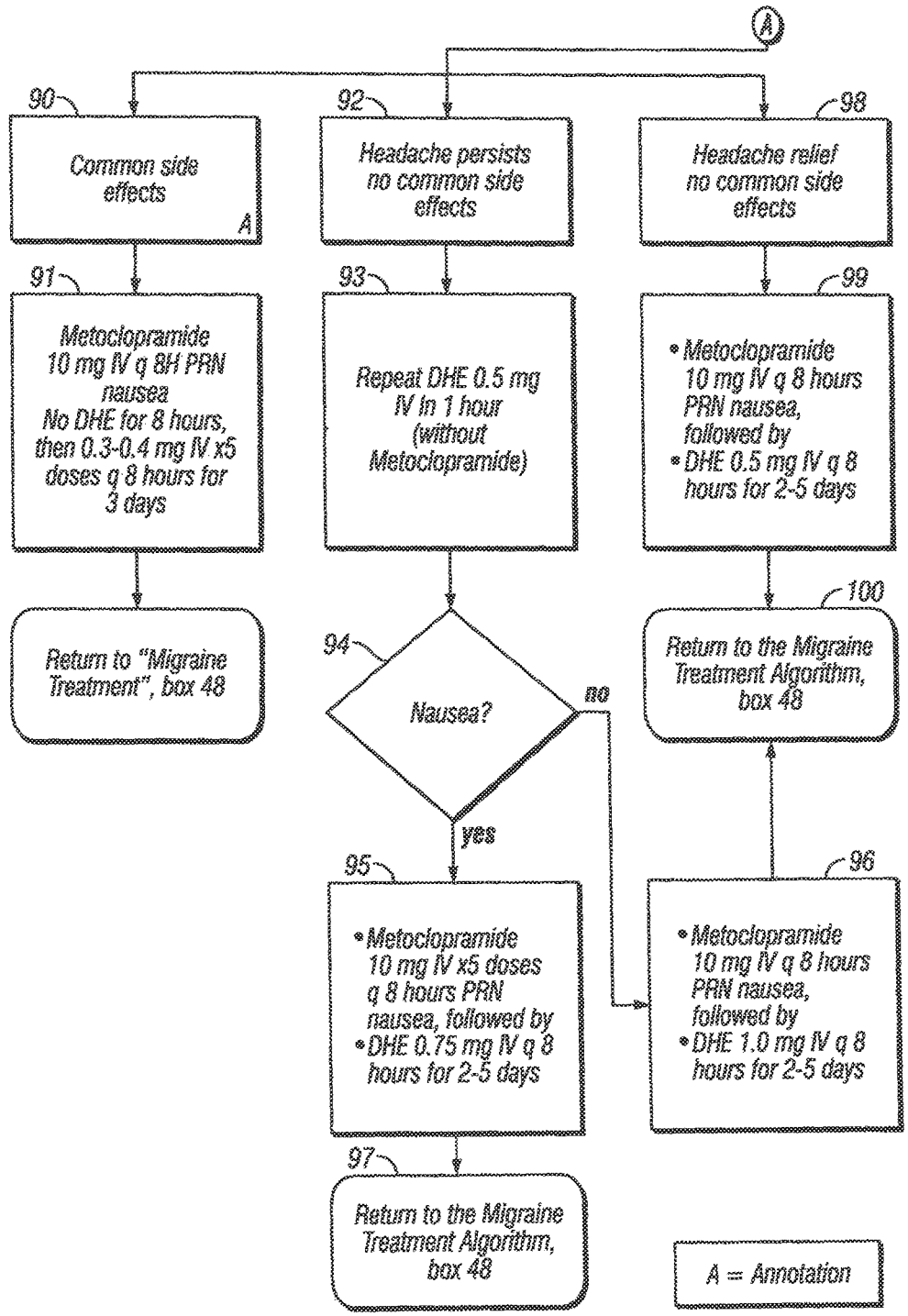

Example 3: Serotonin, Adrenergic and Dopaminergic Receptor Binding by DHE at Concentrations Equivalent to Peak Plasma Concentrations Radioligand receptor binding assays clearly show that DHE exhibits wide ranging pharmacology at multiple receptor sites. (FIGS. 3-5.) For the majority of receptors, DHE achieves significant binding at concentrations equivalent to the IV $C_{max}$ whereas inhaled binding at each dose yields a different profile. In most instances, binding is reduced when non-IV methods are used to administer.

The anti-migraine efficacy of DHE is due to agonist activity at $5\text{-HT}_{1B}$ and $5\text{-HT}_{1D}$ receptors. FIG. 3 shows receptor binding data at various serotonergic receptor subtypes, indicating greater response at several subtypes for intravenous administration at $C_{max}$. The notation "(h)" represents cloned human receptor subtypes. Similar trends were observed for adrenergic and dopaminergic subtypes. Binding at these receptors is demonstrated with 100% binding at $5\text{-HT}_{1B}$ following both 1 mg intravenous and 0.88 mg inhaled dosing. (FIG. 3.) Following inhalation, however, apparent binding at $5\text{-HT}_{1D}$ receptors is lower than IV. The long duration of DHE in circulation beyond $C_{max}$ likely is due to biphasic elimination. (Wyss, P. A., Rosenthaler, J., Nuesch, E., Aellig, W. H. Pharmacokinetic investigation of oral and IV dihydroergotamine in healthy subjects. Eur. J. Clin. Pharmacol. 1991; 41:597-602). These results suggest that maximal receptor binding is not entirely necessary for the duration of clinical response.

As seen in FIGS. 3-5, the IV method of administration with the high $C_{max}$ which resulted in side effects, showed extensive binding at the dopaminergic and adrenergic receptors at concentrations equivalent to the peak plasma spikes ($C_{max}$) resulting from the IV administration method. FIG. 4 shows receptor binding data at adrenergic (left panel) and dopaminergic (right panel) receptors, indicating greater response at several subtypes for intravenous administration at $C_{max}$. The notation "(h)" represents cloned human receptor subtypes and "NS" indicates non-specific binding.

The dopaminergic receptors D1 and D2 are primarily responsible for nausea and emesis. Concentrations equivalent to the peak plasma spikes ($C_{max}$) resulting from the novel administration method that dampened and delayed the peak, as shown in FIG. 2, significantly lowered dopaminergic receptor binding, specifically at D2 and D1, as shown in FIG. 4, with the ultimate result of reducing nausea and emesis in the patients.

Similarly the lowered adrenergic binding shown in FIG. 4, corresponded to less vasoconstriction and lowered blood pressure or cardiovascular excursions in the patients. While receptor binding at the adrenergic and dopaminergic receptors were lower at concentrations equivalent to the peak plasma spikes ($C_{max}$) resulting from the novel administration method, the binding achieved by these administration methods at the serotonin receptors, specifically $5\text{HT}_{1a/d}$ was sufficient to be efficacious for treatment of migraine. (FIG. 3.)

Agonists of $5\text{-HT}_{1B}$ subtype receptors are known to be useful in the treatment of migraine and associated symptoms. $5\text{-HT}_{2B}$ receptors are known to play a triggering role in the onset of migraine. FIG. 5 shows selective agonism at $5\text{-HT}_{1B}$ and $5\text{-HT}_{2B}$ receptors following high concentration control (5 μm), IV at $C_{max}$ (77.6 nM), 4 inhalations at $C_{max}$ (6.25 nM) and at a markedly reduced concentration (0.25 nM). Whereas $5\text{-HT}_{1B}$ agonism is maintained across all concentrations, indicating high potency, agonism is absent for orally-inhaled DHE at the $5\text{-HT}_{2B}$ receptors.

It is noted that all three methods of administration achieve rapid plasma levels within 20 minutes, with concentrations sufficient to bind the serotonin receptors and effect rapid treatment of migraine. (FIG. 2).

Example 4: Pulmonary Administration of DHE Formulations Using a TEMPO™ Inhaler DHE powder is generated using supercritical fluid processes which offer significant advantages in the production of DHE particles for inhalation delivery and produce respirable particles of the desired size in a single step. (see WO2005/025506A2.) A property of processed DHE drug substance is that the supercritical fluid processed crystals have remarkably smooth surfaces with low surface energies and therefore tend to disperse effectively in propellant based systems. A controlled particle size for the microcrystals was chosen to ensure that a significant fraction of DHE would be deposited in the lung.

A blend of two inert and non-flammable HFA propellants were selected as part of formulation development) for the drug product: HFA 134a (1,1,1,2-tetrafluoroethane) and HFA 227ea (1,1,1,2,3,3,3-heptafluoropropane). The finished product contained a propellant blend of 70:30 HFA 227ea: HFA 134a, which was matched to the density of DHE crystals in order to promote pMDI suspension physical stability. The resultant suspension did not sediment or cream (which can precipitate irreversible agglomeration) and instead existed as a suspended loosely flocculated system, which is easily dispersed when shaken. Loosely fluctuated systems are well regarded to provide optimal stability for pMDI canisters. As a result of the formulation's properties, the formulation contained no ethanol and no surfactants/stabilizing agents.

The DHE formulation was administered to patients using TEMPO™, a novel breath activated metered dose inhaler. TEMPO™ overcomes the variability associated with standard pressurized metered dose inhalers (pMDI), and achieve consistent delivery of drug to the lung periphery where it can be systemically absorbed. To do so, TEMPO™ incorporates four novel features: 1) breath synchronous trigger—can be adjusted for different drugs and target populations to deliver the drug at a specific part of the inspiratory cycle, 2) plume control—an impinging jet to slow down the aerosol plume within the actuator, 3) vortexing chamber—consisting of porous wall, which provides an air cushion to keep the slowed aerosol plume suspended and air inlets on the back wall which drive the slowed aerosol plume into a vortex pattern, maintaining the aerosol in suspension and allowing the particle size to reduce as the HFA propellant evaporates, and 4) dose counter—will determine the doses remaining and prevent more than the intended maximum dose to be administered from any one canister. Features 2 and 3 have been shown to dramatically slow the deposition and improve lung deposition of the Emitted Dose (ED), by boosting the Fine Particle Fraction (FPF).

All publications and patent applications cited in this specification are herein incorporated by reference in their entirety as if each individual publication or patent application is specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of providing migraine therapy to a human subject while minimizing one or more drug-induced side effects, said method comprising:

administering via pulmonary administration by oral inhalation a total dose of less than 3.0 mg of dihydroergotamine, or a salt thereof, to the human subject, wherein the dihydroergotamine, or the salt thereof, is administered at a rate that provides a mean peak plasma concentration ($C_{max}$) of dihydroergotamine of less than 20,000 pg/ml within a mean time to $C_{max}$ ($T_{max}$) that is less than 20 minutes after the administration;

wherein the migraine therapy is prophylactic.

2. The method of claim 1, wherein the human subject has at least 2 to 4 headaches per month.

3. The method of claim 2, wherein the at least 2 to 4 headaches per month are severe enough to interfere with daily activity.

4. The method of claim 1, wherein the total dose of the dihydroergotamine, or the salt thereof, ranges from 1.0 mg to 2.0 mg.

5. The method of claim 1, wherein the one or more side effects is selected from the group consisting of nausea, emesis, vasospasm, paresthesia, hypertension, dizziness, anxiety, dyspnea, headache, flushing, diarrhea, rash, increased sweating, cardiac valvulopathy, pleural and retroperitoneal fibrosis, adverse cardiovascular effect, blood pressure instability and arterial constriction.

6. The method of claim 5, wherein the one or more side effects is selected from the group consisting of nausea, emesis, paresthesia and dizziness.

7. The method of claim 6, wherein the one or more side effects is nausea, emesis or both.

8. The method of claim 6, wherein the side effect is nausea.

9. The method of claim 6, wherein the side effect is emesis.

10. The method of claim 6, wherein the side effect is paresthesia.

11. The method of claim 6, wherein the side effect is dizziness.

12. The method of claim 1, wherein the $C_{max}$ of the dihydroergotamine is less than 15,000 pg/ml.

13. The method of claim 1, wherein the $C_{max}$ of the dihydroergotamine is less than 10,000 pg/ml.

14. The method of claim 1, wherein the $C_{max}$ of the dihydroergotamine is less than 7,500 pg/ml.

15. The method of claim 1, wherein the dihydroergotamine, or the salt thereof, is administered by a pressurized metered dose inhaler (pMDI).

16. The method of claim 15, wherein the pMDI is a breath-activated pMDI.

17. The method of claim 1, wherein the dihydroergotamine, or the salt thereof, is administered without administering an anti-emetic to the human subject.

* * * * *